(12) United States Patent
Uttam et al.

(10) Patent No.: US 8,188,112 B2
(45) Date of Patent: May 29, 2012

(54) NAPHTHALAMIDE DERIVATIVES HAVING ANTIPROLIFERATIVE ACTIVITY

(75) Inventors: Surana Uttam, Proteos (SG); Vaidehi Krishnan, Proteos (SG); Anthony Ting, Cleveland, OH (US); Hong Hwa Lim, Proteos (SG)

(73) Assignee: Agency for Science, Technology and Research, Centros (SG)

( * ) Notice: Subject to any disclaimer, the term of this patent is extended or adjusted under 35 U.S.C. 154(b) by 703 days.

(21) Appl. No.: 11/887,064

(22) PCT Filed: Mar. 31, 2005

(86) PCT No.: PCT/SG2005/000105
§ 371 (c)(1),
(2), (4) Date: Apr. 30, 2009

(87) PCT Pub. No.: WO2006/104461
PCT Pub. Date: Oct. 5, 2006

(65) Prior Publication Data
US 2009/0203728 A1    Aug. 13, 2009

(51) Int. Cl.
*A61K 31/439* (2006.01)
*C07D 221/06* (2006.01)
*A61P 35/00* (2006.01)

(52) U.S. Cl. .......................................... 514/296; 546/98
(58) Field of Classification Search .................. None
See application file for complete search history.

(56) References Cited

OTHER PUBLICATIONS

Brana, M. F. et al: "Naphthalimides As Anti-Cancer Agents: Synthesis and Biological Activity" Current Medicinal Chemistry. Anti-Cancer Agents, Bentham Science Publishers, Hilversum, NL, vol. 1, No. 3, Nov. 1, 2001, pp. 237-255.
Ismail, N. et al., "Oxidative Cleavage of Epoxides with Ammonium Molybdate-$H_2O_2$ System: An Efficient Route to α-Hydroxy Ketones," Chemistry Letters 2000, 844-845.
Ranadive, V.B., et al., "Reactions of amines with N-hydroxy-, N-(2,3-epoxypropoxy)-succinimide and naphthalimide," Indian Journal of Chemistry, vol. 34B, Feb. 1995, pp. 102-106.
Nasreen, A, et al., "A Mild and Efficient Stereoselective Synthesis of 1,2-Amino Alcohols Via Catalytic Asymmetric Ring Opening of Epoxide," Research Journal of Chemistry and Environment, vol. 4(3) Sep. (2000).
Okamoto, A. et al., "Site-Selective DNA Alkylation of GG Steps by Naphthaldiimide Derivatives Possessing Enantiomeric Epoxide," Organic Letters 2000, vol. 2, No. 21, 3249-3251.

*Primary Examiner* — Kamal Saeed
(74) *Attorney, Agent, or Firm* — Wilmer Cutler Pickering Hale and Dorr LLP

(57) ABSTRACT

The invention relates to compounds for use in medicine. The compounds are of general formula (I) as disclosed herein and the pharmaceutically acceptable salts, individual isomers and mixtures of isomers thereof, wherein X, X' and X" are independently O or S; Z is N or P; R3 is optional and is selected from the group consisting of optionally substituted $C_{1-8}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ thioalkyl, optionally substituted $C_{5-10}$ aryl, optionally substituted $C_{6-11}$ alkylaryl, optionally substituted $C_{1-6}$ alkylamino, optionally substituted $C_{1-6}$ alkylcarbonyl, optionally substituted $C_{1-6}$ alkylsulfonamino, optionally substituted ($C_1$-$C_6$)alkylsulfinyl, optionally substituted $C_{1-6}$ alkylcarbonylamino, optionally substituted hetero($C_4$-$C_{10}$) aryl, hydroxyl, halogen, cyano, nitro, amino, formyl, and thiol; $R_1$, $R_2$, $R_4$, $R_5$, $R_6$, $R_7$, $R_8$, $R_9$, and $R_{10}$ are independently selected from the group consisting of hydrogen, optionally substituted $C_{1-8}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ thioalkyl, optionally substituted $C_{5-10}$ aryl, optionally substituted $C_{6-11}$ alkylaryl, optionally substituted $C_{1-6}$ alkylamino, optionally substituted $C_{1-6}$ alkylcarbonyl, optionally substituted $C_{1-6}$ alkylsulfonamino, optionally substituted ($C_1$-$C_6$)alkylsulfinyl, optionally substituted $C_{1-6}$ alkylcarbonylamino, optionally substituted hetero($C_4$-$C_{10}$)aryl, hydroxyl, halogen, cyano, nitro, amino, formyl, and thiol; and - - - indicates an optional double bond.

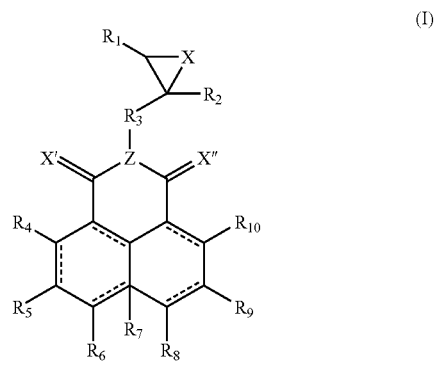

(I)

23 Claims, 14 Drawing Sheets

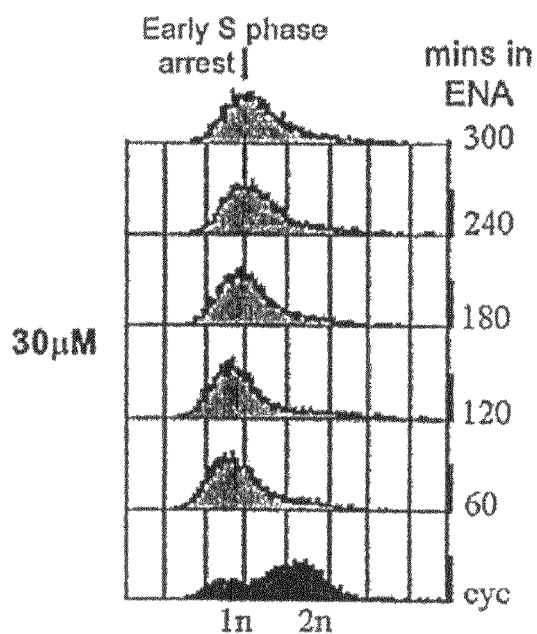
FIG. 2A(i)
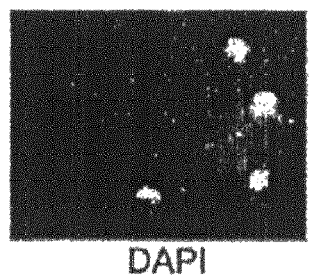
FIG. 2A(ii)
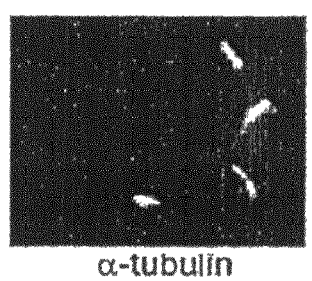
FIG. 2A(iii)
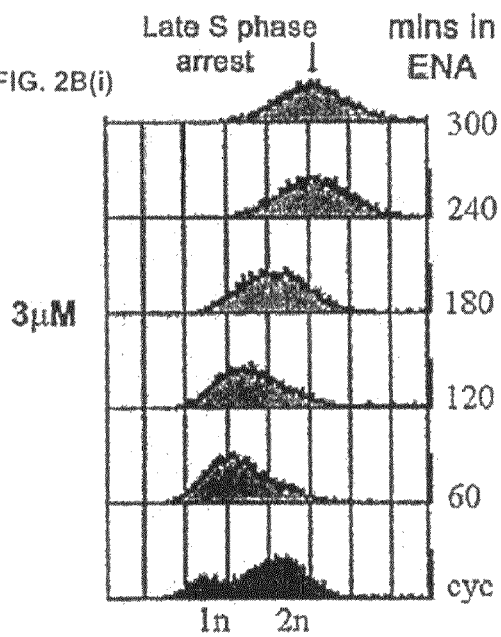
FIG. 2B(i)
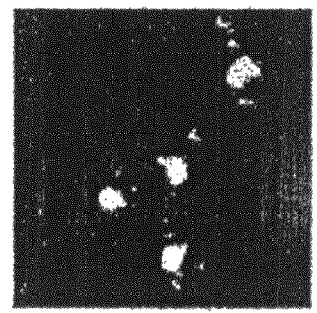
FIG. 2B(ii)
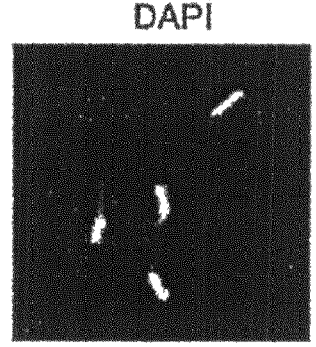
FIG. 2B(iii)

N-(2-CHLOROETHYL)-1,8-NAPHTHALIMIDE ($C_{14}H_{10}ClNO_2$)

1,3-BIS-OXIRANYLMETHYL-4,5-DIPHENYL-1,3-DIHYDRO-IMIDAZOLE-2-ONE ($C_{21}H_{20}N_2O_3$)

N-(2,3-EPOXYPROPYL)-PHTHALIMIDE ($C_{11}H_9NO_3$)

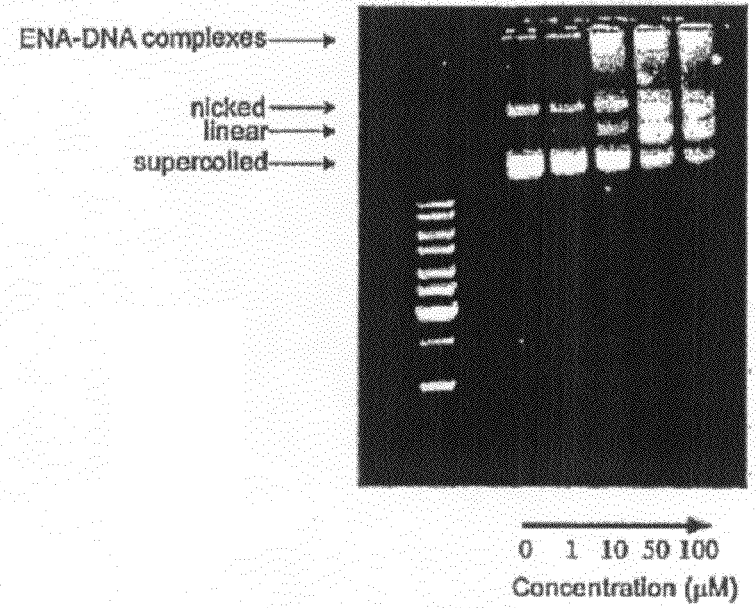
FIG. 4A
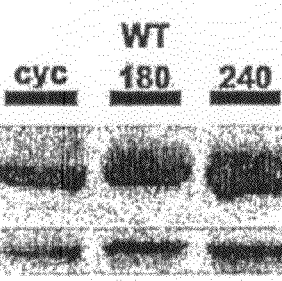
FIG. 4B(i)
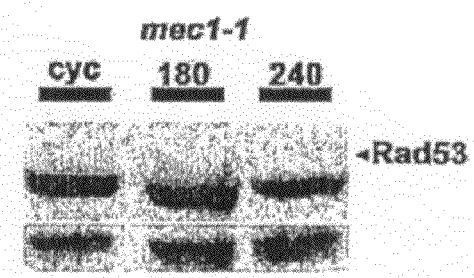
FIG. 4B(ii)

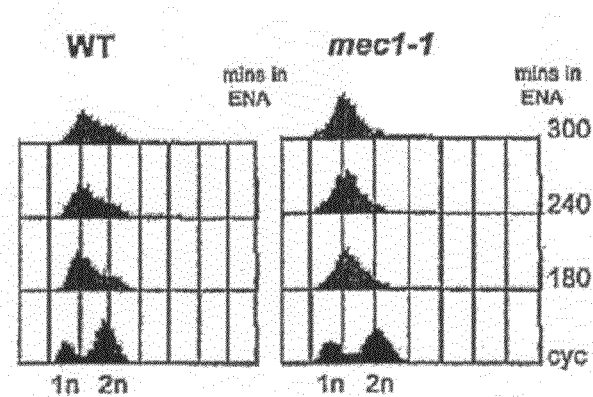
FIG. 5A
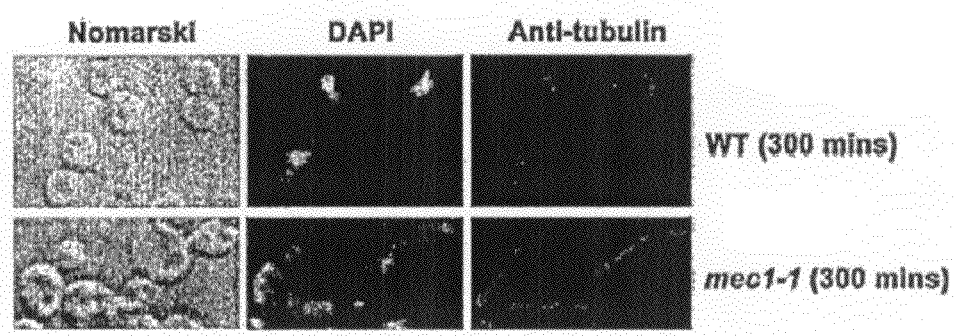
FIG. 5B
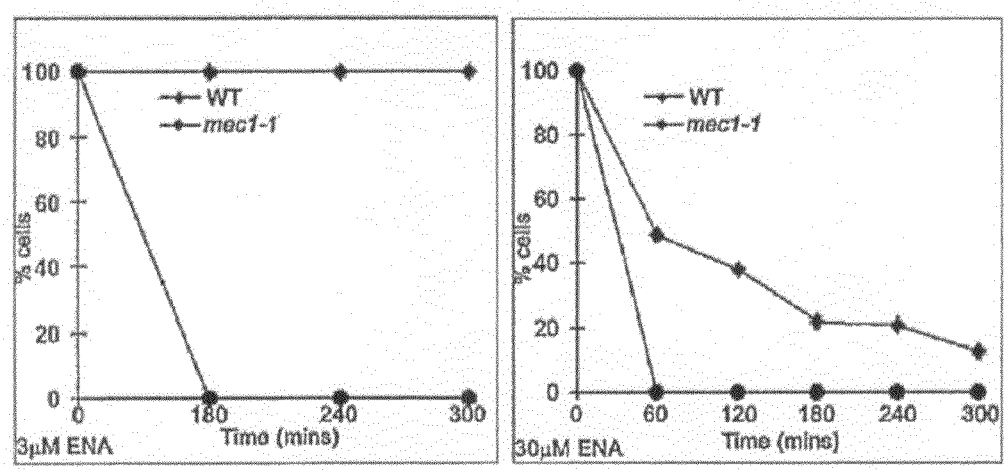
FIG. 5C
FIG. 5D

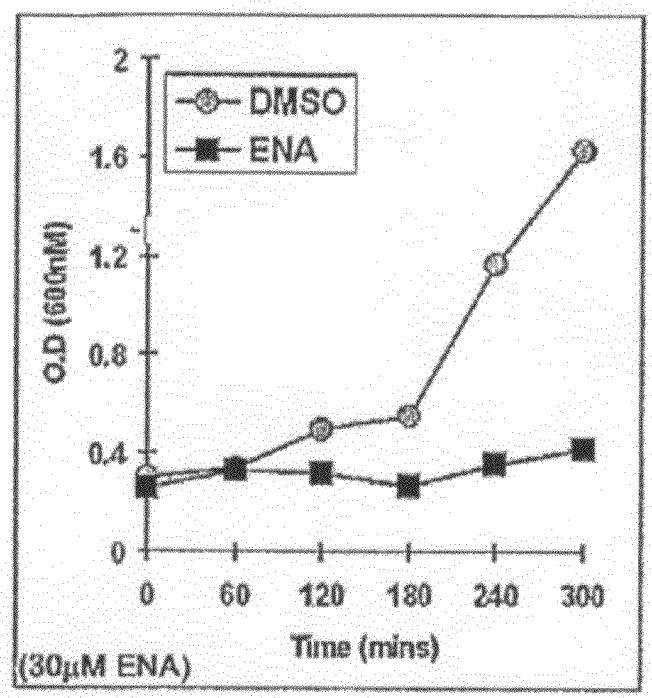
FIG. 10A
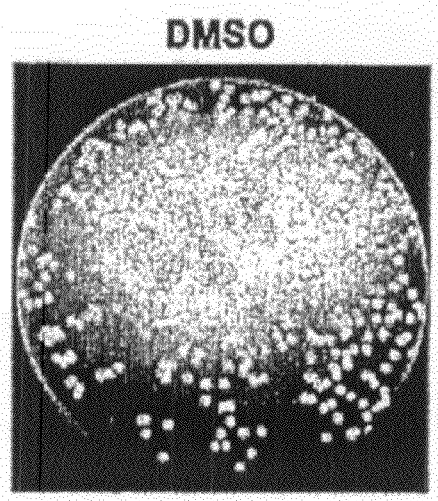
FIG. 10B(i)
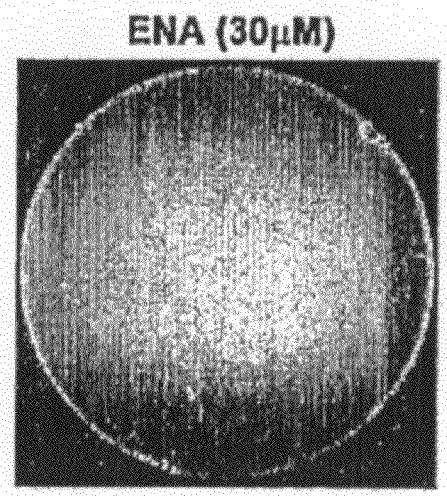
FIG. 10B(ii)

NAPHTHALAMIDE DERIVATIVES HAVING ANTIPROLIFERATIVE ACTIVITY

This application is a U.S. National Phase Application Under 37 U.S.C. §3.71 of International Patent Application No. PCT/SG2005/000105, filed Mar. 31, 2005, which is hereby incorporated by reference into the subject application in its entirety.

TECHNICAL FIELD

The present invention generally relates to naphthalamide derivatives, and associated compositions, having antiproliferative activity towards targeted cells and to methods for their use as therapeutic agents.

All publications cited herein are incorporated by reference in their entirety for all purposes.

BACKGROUND

Mitosis is a cell division process involving a series of cell cycle events in which the nucleus of a cell divides to form two new nuclei, each of which contains a complete copy of the parental chromosomes. The two nuclei ultimately become disconnected and constitute mother and daughter nuclei.

Coordinated execution of cell cycle events is essential for orderly progression through the division cycle and for the maintenance of genome integrity [1]. Any gross departure from this coordination leads to genomic instability associated with many human cancers.

It is known that cellular coordination is imposed, in part, by stress response pathways known as checkpoint controls which ensure that, if a certain event is either interrupted or executed erroneously, the subsequent phase of the cell cycle is not initiated.

During S phase, the genome integrity is mainly monitored by the DNA replication checkpoint [2]. The task of the replication checkpoint is to sense incomplete DNA replication and to respond by delaying the mitotic programme [7]. The Replication Checkpoint also helps maintain stalled replication forks in a state that permits them to resume DNA synthesis [3].

In yeast, Mec1 (homologous to human ATM/ATR kinases) and Rad53 (homologous to human Chk2 kinase) proteins are critical effectors of the replication checkpoint. Like in yeast, phosphoinositide 3-kinase related kinases (PIKKs) ATM (ataxia telangiectasia mutated) and ATR (ATM-Rad3-related) are important stress response regulators during S phase in mammalian cells.

Although the DNA replication checkpoint is known to delay mitosis in response to replication blocks, the molecular mechanisms underlying this mitotic restraint have been relatively ill defined. Recently it has been demonstrated that budding yeast cells avoid mitosis during S phase by repressing the accumulation of the anaphase promoting complex activator, APC Cdc20 [4].

Agents that are capable of interrupting the mitotic programme of targeted cells can be used to initiate cell cycle arrest and/or apoptosis (programmed cell death). Such agents may be used as therapeutic agents for treating conditions associated with the targeted cells.

Normal cells have several checkpoint pathways designed to cope with genotoxic stress that can lead to chromosomal abnormalities. Mutations in cancer cells frequently render them ineffective in order to provide them with proliferative advantage. Cells defective in these pathways are often sensitive to agents that cause genotoxic stress. Such agents may be used as antiproliferation agents to abrogate, inhibit or prevent cell proliferation of cancer cells.

SUMMARY

According to a first aspect of the invention, there is provided a pharmaceutical composition comprising a therapeutically effective amount of a compound of general formula (I):

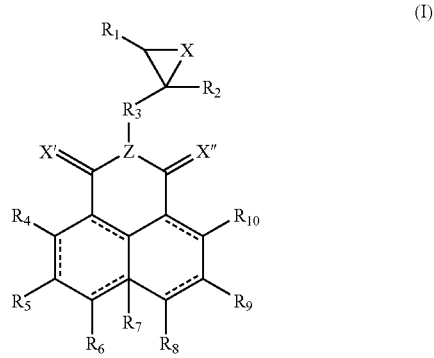

(I)

and the pharmaceutically acceptable salts, individual isomers and mixtures of isomers thereof, in admixture with one or more pharmaceutically acceptable carriers, wherein X, X' and X" are independently O or S;

Z is N or P;

$R_3$ is optional and is selected from the group consisting of optionally substituted $C_{1-8}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ thioalkyl, optionally substituted $C_{5-10}$ aryl, optionally substituted $C_{6-11}$ alkylaryl, optionally substituted $C_{1-6}$ alkylamino, optionally substituted $C_{1-6}$ alkylcarbonyl, optionally substituted $C_{1-6}$ alkylsulfonamino, optionally substituted $(C_1-C_6)$alkylsulfinyl, optionally substituted $C_{1-6}$ alkylcarbonylamino, optionally substituted hetero$(C_4-C_{10})$aryl, hydroxyl, halogen, cyano, nitro, amino, formyl, and thiol;

$R_1$, $R_2$, $R_4$, $R_5$, $R_6$, $R_7$, $R_8$, $R_9$, and $R_{10}$ are independently selected from the group consisting of hydrogen, optionally substituted $C_{1-8}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ thioalkyl, optionally substituted $C_{5-10}$ aryl, optionally substituted $C_{6-11}$ alkylaryl, optionally substituted $C_{1-6}$ alkylamino, optionally substituted $C_{1-6}$ alkylcarbonyl, optionally substituted $C_{1-6}$ alkylsulfonamino, optionally substituted $(C_1-C_6)$alkylsulfinyl, optionally substituted $C_{1-6}$ alkylcarbonylamino, optionally substituted hetero $(C_4-C_{10})$aryl, hydroxyl, halogen, cyano, nitro, amino, formyl, and thiol; and ---indicates an optional double bond.

According to a second aspect of the invention, there is provided a method of reducing the proliferation of a targeted cell, comprising exposing the cell to an effective amount of a compound of formula (I).

The method of the second aspect of the invention may be performed in vitro or in vivo.

According to a third aspect of the invention, there is provided the a compound of formula (I) for use in medicine. In one embodiment the compound is for use as an antiproliferative agent. The third aspect of the invention may also provide a compound of formula (I) for use in inducing apoptosis in a targeted cell.

In one embodiment, the targeted cell may be a eukaryotic cell such as a cancerous cell or a fungal cell.

According to a fourth aspect of the invention, there is provided use of a compound of formula (I), in the manufacture of a medicament for reducing the proliferation of a targeted cell in a patient in need thereof.

In one embodiment the patient is a mammal. The patient may be a human.

In one embodiment, the patient is a cancer patient.

According to a fifth aspect of the invention, there is provided a method of reducing the proliferation of a targeted cell in a patient in need thereof, the method comprising administering to the patient an effective amount of a compound of formula (I).

In one embodiment, the patient may be suffering from cancer. The cancer may be in the form of solid tumors or leukemias.

According to a sixth aspect of the invention, there is provided a kit comprising a pharmaceutical composition as defined in the first aspect, and instructions for exposing a targeted cell to the composition, to thereby reduce proliferation of the targeted cell.

According to a seventh aspect of the invention, there is provided a pharmaceutical composition comprising a therapeutically effective amount of a compound of formula (II):

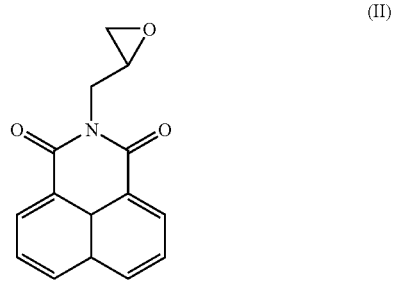

(II)

and the pharmaceutically acceptable salts, individual isomers and mixtures of isomers thereof, in admixture with one or more pharmaceutically acceptable carriers.

In an eighth aspect of the invention there is provided a screening method, the method comprising: (a) providing a cell which overexpresses Cdc20 such that the overexpression causes a reduction in the proliferation of the cell (b) exposing said cell to a candidate compound; and (c) determining whether said candidate compound alleviates the reduction in the proliferation of the cell.

DEFINITIONS & ABBREVIATIONS

The following words and terms (and where appropriate grammatical variants thereof) used herein shall have the meaning indicated:

The phrase "reducing the proliferation of a targeted cell" refers to a reduction in the rate of proliferation and/or a reduction in the amount of proliferation. Thus, for example, the rate of cell division may be reduced and/or the total amount of cell division may be reduced.

The term "proliferation" includes any process (preferably any asexual process) whereby the targeted cell gives rise to one or more further cells. Thus, proliferation includes the generation of new cells by processes such as cell division, binary fission and sporulation etc. The term proliferation also includes the growth of cellular structures such as fungal hyphae where nuclear division is not necessarily linked to cell division.

The term "targeted cell" refers to a cell where a reduction in its proliferation is desired. One or more targeted cells may be present. Thus, there may be a population of targeted cells.

The term "antiproliferative agent" as used herein pertains to a compound which treats a proliferative condition (i.e., a compound which is useful in the treatment of a proliferative condition). Antiproliferative compounds disclosed herein have application in the treatment of cancer, and so the present invention further provides anticancer agents. Antiproliferative compounds disclosed herein have application in inhibiting the growth of a fungus, and so the present invention further provides antifungal agents.

The term "anticancer agent" as used herein, pertains to a compound which treats a cancer (i.e., a compound which is useful in the treatment of a cancer). The anti-cancer effect may arise through one or more mechanisms, including, but not limited to, the regulation of cell proliferation, the inhibition of angiogenesis (the formation of new blood vessels), the inhibition of metastasis (the spread of a tumor from its origin), the inhibition of invasion (the spread of tumor cells into neighboring normal structures), or the promotion of apoptosis.

The term "bioavailability" refers to the ability of a compound to be absorbed by the body after administration. For instance, a first compound has greater bioavailability than a second compound if, when both are administered subcutaneously in equal amounts, the first compound is absorbed into the blood to a greater extent than the second compound.

The terms "cell proliferation", "proliferative condition", "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms, tumors, cancers, leukemias, and infections. Infections may, for example, be caused by fungi or protoctista.

The term "carrier" as used herein denotes a pharmaceutically acceptable solid or liquid filler, diluent or encapsulating material.

The terms "fungus", or "fungi" include a variety of nucleated, sporebearing organisms which are devoid of chlorophyll. Examples include yeasts, mildews, molds, rusts, and mushrooms. Examples of fungi include, but are not limited to *Aspergillus fumigatus, Aspergillus flavus, Aspergillus nidulans, Candida albicans, Candida glabrata, Candida guilliermondii, Candida krusei, Candida lusitaniae, Candida parapsilosis, Candida tropicalis, Cryptococcus neoformans, Issatchenkia orientalis, Coccidioides, Paracoccidioides, Histoplasma, Blastomyces*, and *Neurospora crassa*. The fungi may include fungi of the genus *Candida* (e.g., *C. albicans, C. tropicalis, C. parapsilosis, C. lusitaniae, C. krusei, C. guilliermondii, C. glabrata*, and *C. dubliniensis*).

The term "antifungal agent" as used herein, pertains to a compound which treats fungal conditions and includes a compound which is capable of exhibiting fungistatic or fungicidal activity.

The term "inhibiting the growth of a fungus" includes both fungistatic and fungicidal activity. Fungistatic activity includes any decrease in the rate or amount of growth of a fungal colony. Fungistatic activity may be manifested by a fungus maintaining its present size or failing to colonize the surrounding areas. Fungistatic activity may be a result of inhibition of the fungal reproductive processes. Fungicidal activity generally includes, for example, irradiation of a fungus or fungal colony, killing a fungus or fungal colony or a decrease in the mass or size of a fungus or fungal colony.

The term "antifungal activity" includes inhibiting the growth of a fungus (e.g., fungistatic activity), killing at least a portion of the fungus (e.g., fungicidal activity), limiting the ability of the fungus to reproduce, etc.

The term "protoctista" (or Protista) refers to a number of largely unrelated organisms which are grouped together for convenience. The protoctists are largely unicellular, although many are colonial, and some multicellular. There are plant-like, animal-like ("protozoa"), and fungus-like protoctists. Protozoa includes amoebae and more complex forms such as foraminifera, heliozoans, and radiolarians. Various protoctista cause parasitic infections in animals, in particular protozoa. Common infections include: amoebic dysentery, Chagas disease, sleeping sickness (Trypanosomiasis), malaria Toxoplasmosi, Schistosomiasis and Typhus.

"Cdc20" as used herein refers to the Cdc20 protein or gene as appropriate. The term not only includes the *S. cerevisiae* Cdc20 yeast sequence but includes homologous proteins and genes in other organisms where their overexpression results in a reduction in the survival or proliferation of the cell.

The *S. cerevisiae* Cdc20 yeast sequence may comprise the following nucleotide sequence:

```
tatcaaaaga gcaagtatta caaagaagac taatgccaga aagctctaga gataagggaa atgcagcaat tagcggtaac cgttctgtac tttctattgc gtccccaaca aagctaaaca tactatcttc cgattggtcc agaaaccaag gtaaagtttc taaaaattcg ctaaagagat caagttcact gaacattaga aactccaaac gtcccagttt acaagcctct gccaattcta tttattcaag acctaagatt acaattgggg caccaccgtt aataagacga gattcttcat ttttcaaaga tgaatttgac gctaaaaaag acaaagcaac gttttcggca tactcttctc gttcatatcc aacaattgga tctgagagcg tagtttccca aacatcttta tcgcaaccga caacatctag agaagttgat gagcaattta cagtagctgc ggatagatat attccaattc tacagggagc ttcgcaaaac aaggtcgatc ctgaaacctt acacgaggca ttacctccgc caaacgcgtc gccaatttca cacttaaggg cccagactaa gattgtcttc aaacaaaatg tagctgaagc gtgtgggtta gatatgaata aagaatact acaatacatg ccggaaccac caaaatgctc ttccttgaga caaaaaagct atatcatgaa gaaaagaaca cattatagtt atcagcagga acaaaaaatt cctgatttaa ttaaattaag gaaaatcaat accaatccgg aaagaattct tgatgcacct ggtttccaag acgactttta tttaaacttg ttaagttggt ccaaaaaaaa tgtcttagct atagcactag acactgcatt atatctgtgg aatgccacca ctggggatgt ttccctgtta
```

-continued
```
acggatttcg aaaacaccac aatatgcagc gttacgtggt ctgatgatga ttgtcatatc tctatggcta aagaggatgg gaacaccgaa atttgggacg ttgagaccat gtcattaatt agaactatga gatcaggctt aggtgtccgt atcggttcat tgtcttggtt agatactttg atagctacag gcagtcgtag tggagaaatt caaatcaatg atgtcaggat caaacagcat attgtatcta catgggcaga gcacacaggc gaagtctgcg gtttgagcta taaaagtgac ggattgcaac ttgcatctgg tggtaatgat aacactgtaa tgatttggga taccagaacg tccttgcctc aattttccaa gaagacgcat actgctgctg taaaagcact aagctggtgt ccatattcgc caaatattct agcctctgga ggcggacaaa cagataaaca catccatttt tggaacagta tcacaggtgc acgagttggc tcaatcaata ccggatccca ggtgagctct ttacattggg gccaaagtca tacgtcaacc aatggtggta tgatgaataa agagattgtt gccacaggag gtaatcagag aatgcaatct ctgtttataa ttatgaaaca aaattcaaag ttgcagaagt agttcatgct catgaagcaa gaatatgctg ttctcaattg tcccctgacg gaaccacatt ggccacagtg ggaggagatg
``` or the following amino acid sequence:

```
MPESSRDKGNAAISGNRSVLSIASPTKLNILSSDWSRNQGKVSK

NSLKRSSSLNIRNSKRPSLQASANSIYSRPKITIGAPPLIRRDS

SFFKDEFDAKKDKATFSAYSSRSYPTIGSESVVSQTSLSQPTTS

REVDEQFTVAADRYIPILQGASQNKVDPETLHEALPPPNASPIS

HLRAQTKIVFKQNVAEACGLDMNKRILQYMPEPPKCSSLRQKSY

IMKKRTHYSYQQEQKIPDLIKLRKINTNPERILDAPGFQDDFYL

NLLSWSKKNVLAIALDTALYLWNATTGDVSLLTDFENTTICSVT

WSDDDCHISMAKEDGNTEIWDVETMSLIRTMRSGLGVRIGSLSW

LDTLIATGSRSGEIQINDVRIKQHIVSTWAEHTGEVCGLSYKSD

GLQLASGGNDNTVMIWDTRTSLPQFSKKTHTAAVKALSWCPYSP

NILASGGGQTDKHIHFWNSITGARVGSINTGSQVSSLHWGQSHT

STNGGMMNKEIVATGGNQRMQSLFIIMKQNSKLQK
```

Examples of homologs include:
Human CDC20 (p55CDC/hCDC20) (Cell division cycle 20, seven WD repeat protein that is essential for cell division, interacts with and activates the mitotically phosphorylated form of the anaphase promoting complex, involved in mitotic spindle checkpoint activation);

Human FLJ37927 (Protein containing four WD domains (WD-40 repeats), has moderate similarity to human CDC20, which interacts with and activates the mitotically phosphorylated form of the anaphase promoting complex and is essential for cell division);

Human FZR1 (Fizzy-related protein 1, an activator that binds to the anaphase promoting complex (APC) and promotes its cyclin ubiquitination activity);

Mouse Cdc20 (Protein with very strong similarity to cell division cycle 20 (rat Cdc20), which is essential for cell division and may function in the formation of the mitotic spindle, contains six WD40);

rat Cdc20 (Cell division cycle 20, seven WD repeat protein that is essential for cell division, may function in the formation of the mitotic spindle);

worm fzy-1 (Cdc20, a protein that is required for antero-posterior polarity);

budding yeast CDH1 (protein of the WD (WD-40) repeat family that binds to substrates (CLB2, CLB3, CDC5, HSL1) of the anaphase promoting complex (APC) and targets them for degradation);

Fission Yeast Gene name (slp1) (Cdc20 homolog in fission yeast);

*Candida albicans* CDC20 (Protein containing three WD domains (WD-40 repeats), which may mediate protein-protein interactions, has high similarity to a region of *S. cerevisiae* Cdc20p, which is an activator of anaphase promoting complex required for chromosome segregation and microtubule function at mitosis);

*Drosophila Melanogaster*: Cdc20 homolog is known as Fizzy

Within the term Cdc20 we also include fragments and variants of the *S. cerevisiae* Cdc20 and fragments and variants the aforementioned homologs of *S. cerevisiae* Cdc20.

Such homologs, fragments and variants (including fragments and variants of said homologs) possess qualitative biological activity in common with *S. cerevisiae* Cdc20. Hence, their overexpression results in a reduction of the survival or proliferation of the cell. As will be appreciated from the discussion herein a reduction in the growth of cells may, for example, be measured spectrophotometrically (see for example FIG. 1). Hence, to determine if a putative homolog/fragment/variant possesses qualitative biological activity in common with Cdc20 the growth of a cell overexpressing said putative homolog/fragment/variant can be assayed spectrophotometrically.

The term "fragment" refers to a nucleic acid or polypeptide molecule that encodes a constituent or is a constituent of the full-length Cdc20 gene/polypeptide (or homolog thereof). The fragment possesses qualitative biological activity in common with Cdc20. The fragment may be derived from the full-length Cdc20 or alternatively may be synthesised by some other means, for example chemical synthesis.

The term "variant" as used herein refers to substantially similar sequences. Generally, nucleic acid sequence variants encode a polypeptide which possesses qualitative biological activity in common with Cdc20. Generally, polypeptide sequence variants also possess qualitative biological activity in common with Cdc20. Further, these polypeptide sequence variants may have at least 25%, 30%, 35%, 40%, 45%, 50%, 55%, 60%, 65%, 70%, 75%, 80%, 85%, 90%, 95%, 96%, 97%, 98% or 99% sequence identity to Cdc20 (or to one of its homologs) or to a fragment thereof.

As used herein "sequence identity" refers to the residues in two sequences that are the same when aligned for maximum correspondence over a specified window of comparison by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), *Journal of Molecular Biology*, 48, 443-453).

Further, a variant polypeptide may include analogues, wherein the term "analogue" as used herein with reference to a polypeptide means a polypeptide which is a derivative of Cdc20 (including a homolog thereof), which derivative comprises addition, deletion, substitution of one or more amino acids, such that the polypeptide retains substantially the same biological activity as Cdc20.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

The variants, fragments and homologs can be located and isolated using standard techniques in molecular biology, without undue trial and experimentation.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), *Journal of Molecular Biology*, 48, 443-453). Using GAP with the following settings for DNA sequence comparison: GAP creation penalty of 5.0 and GAP extension penalty of 0.3.

Nucleic acid molecules may be aligned to each other using the Pileup alignment software, available as part of the GCG program package, using, for instance, the default settings of gap creation penalty of 5 and gap width penalty of 0.3.

The terms "effective amount", "therapeutically effective amount" and "pharmaceutically effective amount" are used interchangeably herein and pertain to an amount of a therapeutic agent to treat, ameliorate, or prevent a desired disease or condition, or to exhibit a detectable therapeutic or preventative effect. The effect can be detected by, for example, chemical markers or antigen levels. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

As used herein, the term "pharmaceutically acceptable salt" refers to those salts which retain the biological effectiveness and properties of the active compound of the antimicrobial composition, which are not otherwise undesirable. A thorough discussion of pharmaceutically acceptable salts is available in Remington's Pharmaceutical Sciences (Mack Pub. Co., N.J. 1991).

As used herein the term "treatment", refers to any and all uses which remedy a disease state or symptoms, prevent the establishment of disease, or otherwise prevent, hinder, retard, or reverse the progression of disease or other undesirable symptoms in any way whatsoever.

By a "candidate compound" we include can be any molecule or combination of more than one molecule. Examples of "candidate compounds" may include synthetic small molecule agents, chemical compounds, chemical combinations, and salts thereof as well as natural products, such as plant extracts. Other molecules that can be identified using the screens of the invention include proteins and peptide fragments, peptides, nucleic acids and oligonucleotides, carbohydrates, phospholipids and other lipid derivatives. In a preferred embodiment a library of compounds may be screened.

As used herein the term "comprising" means "including, but not necessarily solely". Variations of the word "comprising", such as "comprise" and "comprises", have correspondingly varied meanings. Thus, for example, a composition "comprising" X may consist exclusively of X or may include one or more additional components.

As used herein, the term "about", in the context of concentrations of components of the formulations, typically means +/−5 or 10% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges.

As used herein, the term "alkyl group" includes within its meaning monovalent ("alkyl") and divalent ("alkylene") straight chain or branched chain saturated aliphatic groups having from 1 to 10 carbon atoms, eg, 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "alkenyl group" includes within its meaning monovalent ("alkenyl") and divalent ("alkenylene") straight or branched chain unsaturated aliphatic hydrocarbon groups having from 2 to 10 carbon atoms, eg, 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butenyl, 1,3-butadienyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenal, 1-heptenyl, 2-heptenyl, 3-heptenyl, 1-octenyl, 1-nonenyl, 1-decenyl, and the like.

The term "alkynyl group" as used herein includes within its meaning monovalent ("alkynyl") and divalent ("alkynylene") straight or branched chain unsaturated aliphatic hydrocarbon groups having from 2 to 10 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynol, 1-heptynyl, 2-heptynyl, 1-octynyl, 2-octynyl, 1-nonyl, 1-decynyl, and the like.

The term "halogen" or variants such as "halide" or "halo" as used herein refers to fluorine, chlorine, bromine and iodine.

The term "alkoxy" as used herein refers to straight chain or branched alkyloxy groups. Examples include methoxy, ethoxy, n-propoxy, isopropoxy, tert-butoxy, and the like.

The term "optionally substituted" as used herein means the group to which this term refers may be unsubstituted, or may be substituted with one or more groups independently selected from alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynol, acylamino, diacylamino, acyloxy, alkylsulfonyloxy, heterocyclooxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, alkylheteroaryl, cyano, cyanate, isocyanate, —C(O)NH(alkyl), and —C(O)N(alkyl)$_2$.

The term "hydroxyl" means —OH.
The term "thiol" means —SH.
The term "cyano" means —CN.
The term "nitro" means —NO$_2$.
The term "amino" means —NH$_2$.

The term "heteroatom" as used herein means an atom of any element other than carbon or hydrogen. Examples include N, O, S and P.

The term "thioalkyl" refers to an alkyl group, as defined above, having a sulfhydryl or thioether group attached thereto. Examples include —S-alkyl, —S-alkenyl, and —S-alkynyl.

The term "Aryl" refers to a monovalent mono-, bi- or tricyclic aromatic hydrocarbon moieties of five to ten carbon ring atoms. Exemplary aryl groups include phenyl and naphthyl. The aryl group can optionally be substituted with one or more substituents. Typical substituents for aryl groups include alkyl, haloalkyl, heteroalkyl alkoxy, halo, cycloalkyl, heteroaryl and another aryl group. Exemplary aryl groups include phenyl, 1-naphthyl, and 2-naphthyl, anthracenyl, and the like.

The term "alkaryl" refers to an aryl group in which the aromatic ring is substituted with alkyls as defined above.

The term "carbonyl" means —C=O.

The term "alkylcarbonyl" refers to an alkyl as defined above bonded to a carbonyl as defined above.

The term "alkylamino" refers to an alkyl as defined above bonded to an amino as defined above.

The term "alkylsulfoamino" refers to a —SO$_2$— group bonded to an alkyl as defined above and an amino as defined above.

The term "alkylsulfinyl" refers to a —SO— group bonded to an alkyl as defined above and an amino as defined above.

The term "alkylcarbonylamino" refers to a carbonyl as defined above bonded to an alkyl as defined above and an amino as defined above.

The term "heteroaryl" as used herein refers to an aryl moiety having one or more heteroatoms. Exemplary heteroaryls include pyrrolyl, triazolyl, pyridinyl, isoxazolyl, pyrimidinyl, thienyl, furyl, thiadiazoyl, pyrazoyl, isothiazolyl, thiazolyl, oxazolyl, imidazolyl, pyridazinyl, oxadiazolyl and pyrazinyl.

In the context of this invention the term "administering" and variations of that term including "administer" and "administration", includes contacting, applying, delivering or providing a compound or composition of the invention to an organism, or a surface by any appropriate means.

In the context of this specification, the term "mammal" includes, without limitation rats, mice, cats, dogs, horses, cattle, cows, pigs, rabbits, non-human primates, and humans.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the terms "therapeutically effective amount" and "diagnostically effective amount", include within their meaning a sufficient but nontoxic amount of a compound or composition of the invention to provide the desired therapeutic or diagnostic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

BRIEF DESCRIPTION OF THE DRAWINGS

The accompanying drawings serve to explain the principles of the disclosed biological studies. It is to be understood, however, that the drawings are designed for purposes of illustration only, and not as a definition of the limits of the invention.

FIG. 2 depicts DNA content measurement and cell division analysis of wild-type yeast cells treated with the COMPOUND (IX) compound in accordance with a disclosed embodiment.

FIG. 4 depicts measurement of the binding of the COMPOUND (IX) to DNA and one means by which it induces RAD53 phosphorylation in accordance with a disclosed embodiment. (Cyc denotes cycling.)

FIG. 5 depicts cell division and growth of mec1-1 cells treated with the Compound (IX).

FIG. 10 depicts the effect of treating a *Candida albicans* strain with the Compound (IX).

DETAILED DISCLOSURE OF EMBODIMENTS

Figure 1:
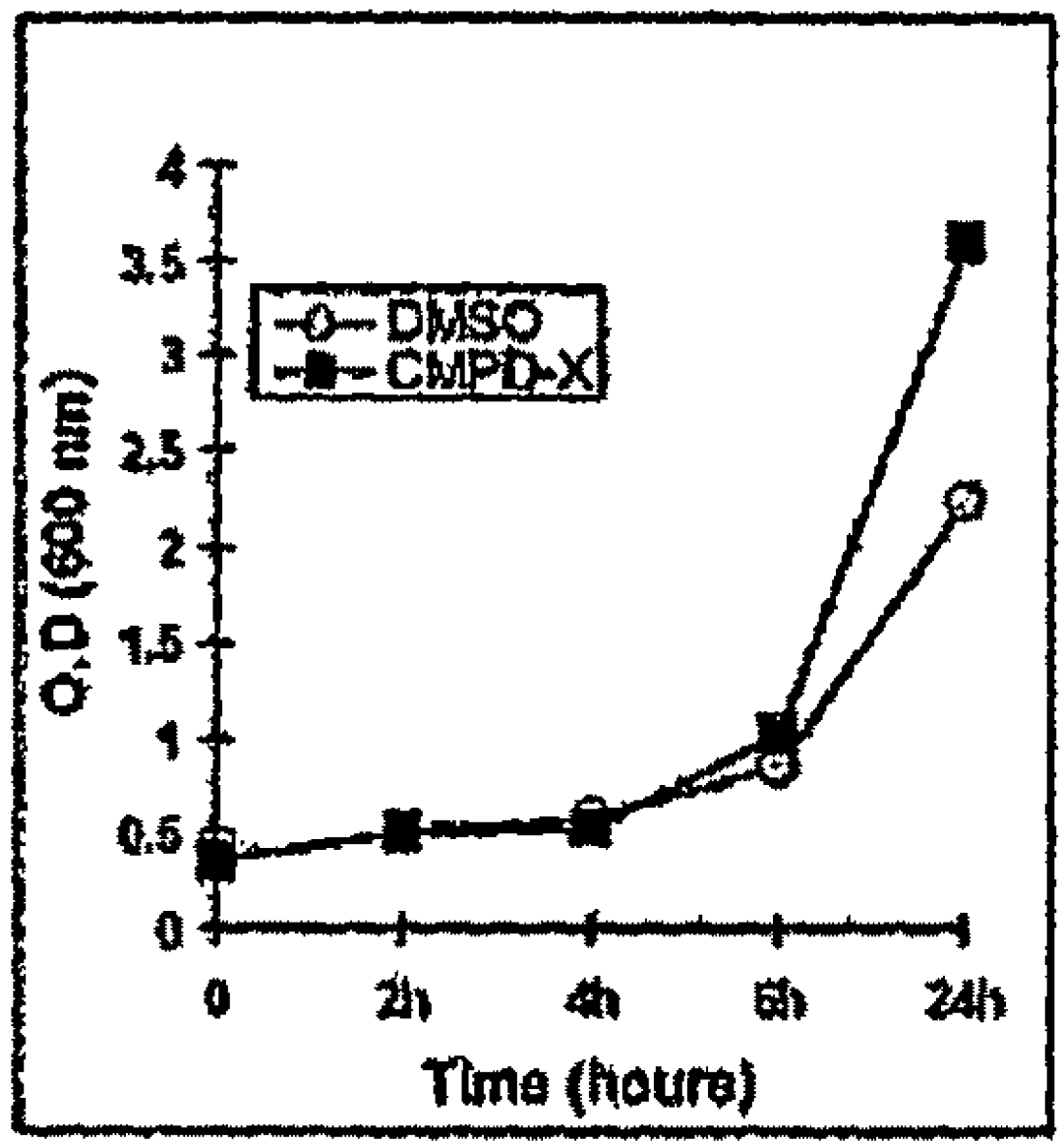
FIG. 1 is a graph plotting the survival of US1392 yeast mutant cells treated with the compound (IX) and in DMSO in accordance with a disclosed embodiment of the invention.

Exemplary, non-limiting embodiments of a composition comprising naphthalamide derivatives compounds capable of inhibiting cell proliferation in targeted cells will now be disclosed.

The inventors have surprisingly found that the active compounds as disclosed herein exhibit cytotoxicity in vitro to certain fungal colonies and cancer cell lines. Accordingly, the active compounds disclosed herein can be used as antifungal agents and as anticancer agents for administration to mammals.

The Active Compounds

The active compounds may be represented by the following general formula (I):

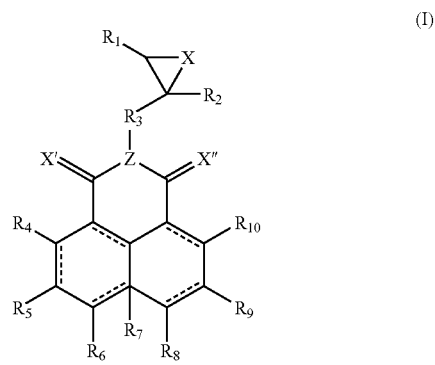

and the pharmaceutically acceptable salts, individual isomers and mixtures of isomers thereof, wherein X, X' and X" are independently O or S;

Z is N or P;

$R_3$ is optional and is selected from the group consisting of optionally substituted $C_{1-10}$ alkyl, optionally substituted $C_{2-8}$ alkenyl, optionally substituted $C_{2-8}$ alkynyl, optionally substituted $C_{1-6}$ alkoxy, optionally substituted $C_{1-6}$ thioalkyl, optionally substituted $C_{5-10}$ aryl, optionally substituted $C_{6-11}$ alkylaryl, optionally substituted $C_{1-6}$ alkylamino, optionally substituted $C_{1-6}$ alkylcarbonyl, optionally substituted $C_{1-6}$ alkylsulfonamino, $(C_1-C_6)$ alkylsulfinyl, optionally substituted $C_{1-6}$ alkylcarbonylamino, optionally substituted hetero $(C_4-C_{10})$aryl, hydroxyl, halogen, cyano, nitro, amino, formyl, and thiol;

$R_1$, $R_2$, $R_4$, $R_5$, $R_6$, $R_7$, $R_8$, $R_9$, and $R_{10}$ are independently selected from the group consisting of hydrogen, optionally substituted $C_{1-10}$ alkyl, optionally substituted $C_{2-8}$ alkenyl, optionally substituted $C_{2-8}$ alkynyl, optionally substituted $C_{1-6}$ alkoxy, optionally substituted $C_{1-6}$ thioalkyl, optionally substituted $C_{5-10}$ aryl, optionally substituted $C_{6-11}$ alkylaryl, optionally substituted $C_{1-6}$ alkylamino, optionally substituted $C_{1-6}$ alkylcarbonyl, optionally substituted $C_{1-6}$ alkylsulfonamino, ($C_1$-$C_6$) alkylsulfinyl, optionally substituted $C_{1-6}$ alkylcarbonylamino, optionally substituted hetero($C_4$-$C_{10}$) aryl, hydroxyl, halogen, cyano, nitro, amino, formyl, and thiol; and ---indicates an optional double bond.

In one embodiment, X, X' and X" are independently O or S. In one embodiment, X, X' and X" are all O.

In one embodiment, Z is N.

In one embodiment, $R_1$, $R_2$, $R_3$, $R_4$, $R_5$, $R_6$, $R_7$, $R_8$, $R_9$, and $R_{10}$ are independently selected from the group consisting of optionally substituted $C_{1-8}$ alkyl, optionally substituted $C_{2-8}$ alkenyl, optionally substituted $C_{2-8}$ alkynyl, optionally substituted $C_{1-4}$ alkoxy, optionally substituted $C_{1-4}$ thioalkyl, optionally substituted $C_{6-8}$ aryl, optionally substituted $C_{7-9}$ alkylaryl, optionally substituted $C_{1-4}$ alkylamino, optionally substituted $C_{1-4}$ alkylcarbonyl, optionally substituted $C_{1-4}$ alkylsulfonamino, ($C_1$-$C_6$) alkylsulfinyl, optionally substituted $C_{1-4}$ alkylcarbonylamino, and optionally substituted hetero ($C_4$-$C_8$) aryl.

In one embodiment, $R_1$, $R_2$, $R_3$, $R_4$, $R_5$, $R_6$, $R_7$, $R_8$, $R_9$, and $R_{10}$ are independently selected from the group consisting of optionally substituted $C_{1-6}$ alkyl, optionally substituted $C_{2-6}$ alkenyl, optionally substituted $C_{2-6}$ alkynyl, optionally substituted $C_{1-2}$ alkoxy, optionally substituted $C_{1-2}$ thioalkyl, optionally substituted $C_{6-7}$ aryl, optionally substituted $C_{1-2}$ alkylamino, optionally substituted $C_{1-2}$ alkylcarbonyl, optionally substituted $C_{1-2}$ alkylsulfonamino, ($C_1$-$C_4$) alkylsulfinyl, optionally substituted $C_{1-2}$ alkylcarbonylamino, and optionally substituted hetero ($C_4$-$C_6$) aryl.

In one embodiment, $R_1$, $R_2$, $R_3$, $R_4$, $R_5$, $R_6$, $R_7$, $R_8$, $R_9$, and $R_{10}$ are independently selected from the group consisting of optionally substituted $C_{1-4}$ alkyl, optionally substituted $C_{2-4}$ alkenyl, and optionally substituted $C_{2-4}$ alkynyl.

In one embodiment, the compound has the general formula (II):

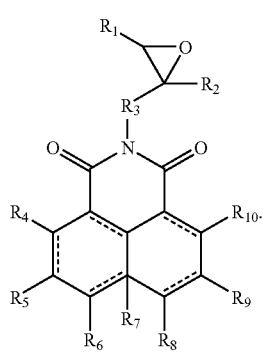

(II)

In one embodiment, the compound has the general formula (III):

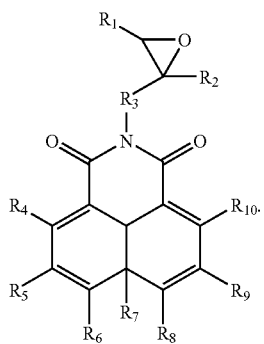

(III)

In one embodiment, the compound has the general formula (IV):

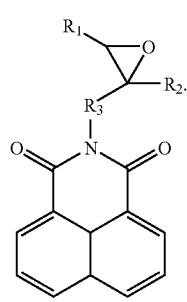

(IV)

In one embodiment, the compound has the general formula (V):

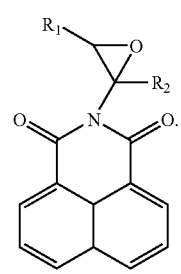

(V)

In one embodiment, the compound has the formula (VI):

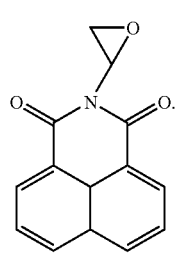

(VI)

In one embodiment, the compound has the formula (VII):

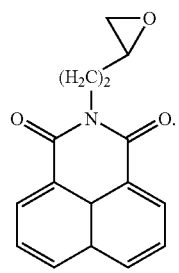

(VII)

In one embodiment, the compound has the formula (VIII):

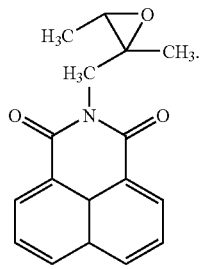

(VIII)

In one embodiment, the compound has the formula (IX):

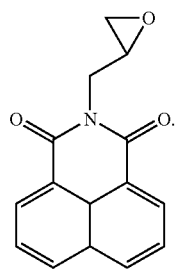

(IX)

In this embodiment, the compound of formula (IX) has an IUPAC name of 2-(oxiran-2-ylmethyl)-1H-benzo[de]isoquinoline-1,3(2H)-dione. The trivial name is 2-methylepoxy-1,8 naphthalamide.

Other embodiments may be compounds selected from the group consisting of: 2-(2-oxiran-2-ylethyl)-1H-benzo[de]isoquinoline-1,3(2H)-dione; 2-[(3-methyloxiran-2-yl)methyl]-1H-benzo[de]isoquinoline-1,3(2H)-dione; 2-[(2,3-dimethyloxiran-2-yl)methyl]-1H-benzo[de]isoquinoline-1,3(2H)-dione; 2-(oxiran-2-ylmethyl)-1,3-dioxo-2,3-dihydro-1H-benzo[de] isoquinolin-5-yl nitrite; and 2-(oxiran-2-ylmethyl)-1,3-dioxo-2,3-dihydro-1H-benzo[de]isoquinoline-5,8-diyldinitrite.

It has been surprisingly found that the disclosed active compounds are effective at inducing cell-cycle arrest and as such may find utility as potent anticancer and antifungal agents. Particularly preferred active compounds that are anticancer and antifungal agents are compounds comprising a 1,8-naphthalamide moiety and an epoxide moiety, connected by a alkyl linker.

Synthesis of Epoxy 1,8-Naphthalamides

The compounds disclosed herein may be synthesised utilizing known methodologies disclosed in texts well known to those skilled in the art such as *Advanced Organic Chemistry*, 3rd Ed.; John Wiley: New York (1985) or J. March, *Advanced Organic Chemistry—Reactions, Mechanisms and Structure*, John Wiley & Sons, New York, 1992.

Generally a 1,8-naphthalic anhydride (III) and an epoxy alkylamine (IV) are mixed in an organic solvent mixture and refluxed to produce the active compounds. An Exemplary schema for the synthesis of compound (IX) is as follows:

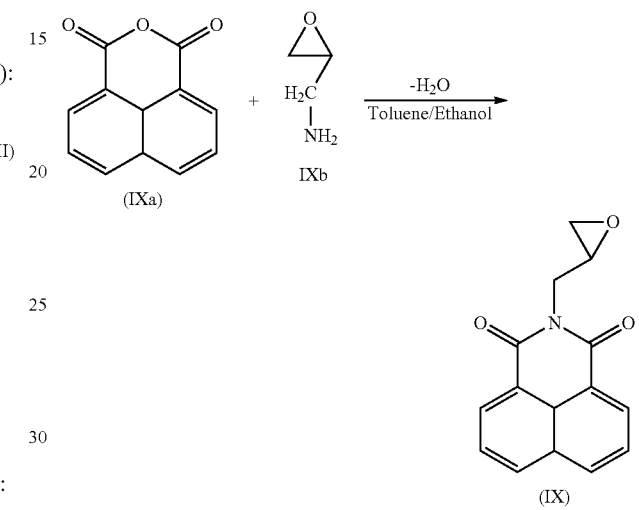

The reactant (IXA) is 1,8-naphthalic anhydride and the reactant (IXB) is 2-methylamine epoxide. Usually, the reactants (IXA) and (IXB) are used in a stoichiometric ratio, but an excess of one component or the other may be advantageous.

The reaction temperature is in general from 0° C. to 150° C., advantageously below the boiling range of the solvent.

An organic solvent is used for refluxing reactants (IXA) and (IXB). Exemplary organic solvents are ethanol, dimethylformamide, toluene and mixtures thereof. In a preferred embodiment, the organic solvent is toluene-ethanol in a 4:1 ratio.

The mixture is refluxed and monitored, for example, by thin-layer chromatography. The resulting mixture is filtered and evaporated.

The reactant 1,8-naphthalic anhydride (1×A) is a known compound and can be purchased commercially from a chemical supplier such as Anshan HIFI Chemical Co. Ltd of China.

The 2-methylamine epoxide (IXB) can be synthesized by heating 2-methylepoxy (IUPAC 2-methyloxirane) at a temperature in the range of 60° C.-80° C. in the presence of aqueous ammonia ($NH_3$) at a pressure of in the range of 1-2 bar (100-200 kPa). 2-methylepoxy and $NH_3$ are commercially available from a number of sources such as The Dow Chemical Company of the United States of America or Sumitomo Chemical Company, Limited of Osaka, Japan.

The compound (IX) can be converted by conventional methods into further derivatives so that the substitution pattern may be varied in a wide range.

Active Compound Salts

In some forms, it will be desirable to formulate the active compounds in pharmaceutically acceptable salt form, generally to improve the solubility and bioavailability and to provide an active drug that is capable of being assimilated readily.

The active compounds form pharmaceutically acceptable salts with both organic and inorganic acids. Suitable physiologically tolerated acids for salt formation are organic and inorganic acids, such as hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like.

The salts are prepared by contacting a free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose.

The free base forms differ from their respective salt forms somewhat in certain physical properties such as solubility in polar solvents, but the salts are otherwise equivalent to their respective free base forms for purposes of the invention.

The active compounds can exist in unsolvated as well as solvated forms, including hydrated forms. Such salt forms of the active compound can be provided or mixed prior to use with a physiologically acceptable solvent such as water or ethanol.

Pharmaceutically Acceptable Carriers

The active compounds disclosed herein may include a conventional pharmaceutical carrier or excipient, and in addition, may include other medicinal agents, pharmaceutical agents, carriers, adjuvants, etc. Examples of suitable pharmaceutical carriers include phosphate buffered saline solutions, water, emulsions, such as oil/water emulsions, various types of wetting agents, sterile solutions etc. Other suitable pharmaceutical carriers are described in Remington's Pharmaceutical Sciences, Mack Publishing Company, a standard reference text in this field, or in U.S. Pharmacopeia National Formulary, 1857-1859, (1990). Compositions comprising such carriers can be formulated by conventional methods.

Mode of Administration

Administration of the active compounds disclosed herein, in pure form or in an appropriate pharmaceutical composition, can be carried out via any of the acceptable mode of administration or pharmaceutically acceptable means of delivery. The modes of administration and pharmaceutically acceptable means of delivery include, but are not limited to, oral, nasal, parenteral, topical or transdermal administration or delivery in the form of solid, semi-solid, lyophilized powder, or liquid dosage forms. The dosage forms include tablets, suppositories, pills, soft elastic and hard gelatin capsules, powders, solutions, suspensions, or aerosols, or the like, preferably in unit dosage forms suitable for simple administration of precise dosages.

Oral Administration

In oral administration of the disclosed active compounds, may be effected by preparing a mixture of the disclosed active compounds with an inert diluent or with an assailable edible carrier, or they may be enclosed in hard or soft shell gelatin capsules, or they may be compressed into tablets, or they may be incorporated directly with the food of the diet. For oral therapeutic administration, the disclosed active compounds may be incorporated with excipients and used in the form of ingestible tablets, buccal tables, troches, capsules, elixirs, suspensions, syrups, wafers, and the like. Such compositions and preparations may contain the active compounds, in an amount by weight percent, selected from the group consisting of: about 0.1% to about 70%; about 0.5% to about 65%; about 1% to about 60%; about 2% to about 55%; and about 3% to about 50%.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Parenteral and Intraperitoneal Administration

The active compounds disclosed herein may be administered parenterally or intraperitoneally. Solutions of the disclosed active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Topical Administration

For topical applications, the active compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

The composition suitable for topical administration may comprise an amount of active compounds by weight in the range selected from the group consisting of: about 1% to about 80%; 1% to about 70%; 1% to about 60%; 2% to about 50%; and 3% to about 50%.

Topical administration is a suitable administration route when the active compounds are being used as antifungal agent for treating a fungal related condition.

Administration Dosage

The active compounds in pharmaceutically acceptable form are administrated in a therapeutically effective amount which will vary depending upon a variety of factors including the activity of the specific compounds employed; the metabolic stability and length of action of the compounds; the age, body weight, general health, sex and diet of the patient; the mode and time of administration; the rate of excretion; the drug combination; the severity of the particular disease states; and the patient undergoing treatment.

Active Compounds as a Therapeutic Agent

It has been surprisingly found that the active compounds of general formula (I) are capable of arresting mitosis of targeted cell lines. Apoptosis of the targeted cells may also occur. Accordingly, the active compounds can be used to treat diseases and conditions associated with the undesired proliferation of targeted cells.

Additionally, the active compounds may find utility in vitro. For instance, the compounds may find utility in controlling the growth of undesired cells, such as fungal growth. The compounds may find utility as a research tool, for instance in studying the mechanism of the DNA replication checkpoint.

The active compounds of the invention may be used to reduce the proliferation of a targeted cell.

In one embodiment, the targeted cell undergoes cell cycle arrest such as S-phase arrest. The arrest may be reversible or irreversible.

In one embodiment the targeted cell, or one or more of its progeny, dies as a result of exposure of the targeted cell to a compound of the invention. In one embodiment, the targeted cell, or one or more of its progeny, undergoes apoptosis.

By a "reduction in the proliferation" of a targeted cell (and similar expressions) we include where there is a reduction in the number of, or rate of, generation of progeny cells arising from the targeted cell (e.g. whether as daughter, grand-daughter, great-grand-daughter cells etc.). Where, nuclear division is not necessarily accompanied by cellular division (e.g. hyphal growth), the term "reduction in the proliferation" may refer to, for example, a reduction in fungal colony growth whether in terms of rate or amount of fungal growth.

As discussed herein, the active compounds of the invention are envisaged as being useful in the treatment of patients suffering from a proliferation of abnormal or unwanted cells. Suitably, the anti-proliferative effect of the compounds of the invention is specific for the targeted cells, that is the targeted cells are more sensitive to the anti-proliferative effect of the compounds of the invention than the non-targeted cells (e.g. "wild-type" cells which are not checkpoint deficient). Hence, where the patient is a cancer patient, the cancerous cells are effected to a greater extent than the patient's non-cancerous cells. As indicated in the Examples section below such an effect was observed in vitro for compound IX of the invention.

The targeted cell may be a eukaryotic cell which may be an animal cell, a plant cell, a fungal cell or a protoctistan cell.

In one embodiment the target cell is a replication checkpoint deficient cell which is deficient in one or more checkpoint pathways, eg Chk1 or Chk2 deficient. For example, Chk1 is aberrant in Endometrial, Gastric and Colorectal carcinomas whilst Chk2 is aberrant in carcinomas of the breast, colon, lung, bladder, ovary, and vulva, sarcomas, lymphomas (AML, NHL), and Li-Fraumeni syndrome (Chk1 and Chk2 kinases in checkpoint control and cancer. Bartek J and Lukas J, Cancer Cell: May 2003, Vol 3, pg 421-429). Thus, in one embodiment of the invention the cell is Check 1 or Check 2 deficient. In one embodiment the cell is Check 1 and Check 2 deficient.

In one embodiment the target cell is a cancer cell.

In one embodiment the target cell is an amoeba. Because amoeba lack replication checkpoints amoeba are likely to be a useful target for the compounds of the invention.

In one embodiment the target cell is a fungal cell, such as a yeast cell.

Active Compounds as Anticancer Agents

The active compounds of general formula (I) have been found to irreversibly arrest mitosis in cancer cell lines. The inventors contemplate that the active compounds and structurally related species may be used to treat, prevent or ameliorate cancers, particularly cancers that are characterized to be checkpoint deficient. For example, Chk1 is aberrant in Endometrial, Gastric and Colorectal carcinomas whilst Chk2 is aberrant in carcinomas of the breast, colon, lung, bladder, ovary, and vulva, sarcomas, lymphomas (AML, NHL), and Li-Fraumeni syndrome (Chk1 and Chk2 kinases in checkpoint control and cancer. Bartek J and Lukas J, Cancer Cell: May 2003, Vol 3, pg 421-429).

Advantageously, it is expected that the active compounds can be used as anticancer agents. It is contemplated that cancers which may be treated include solid tumors and leukemias (for example B cell, mixed cell, null cell, T cell, T-cell chronic, HTLV-II-associated, lymphocytic acute, lymphocytic chronic, mast cell, and myeloid leukemias, melanoma, fibrosarcoma, osteosarcoma, neuroblastoma, neurofibroma, sarcoma (for example Ewing, experimental, Kaposi, and mast cell sarcomas). The cancer may be one of the bone, breast, digestive system, colorectal, liver, pancreatic, pituitary, testicular, central nervous system, lung, urogenital system or prostate. The tumor may be benign or malignant, typically it will be malignant. The tumor may be a primary or secondary tumor and may be metastatic.

The active compounds when administered as anticancer agents in medicament form may be administered on their own or in combination with other anti-cancer treatments such as in conjunction with chemotherapy or radiotherapy.

As will be further described below, an unexpected effect in vitro was observed against HeLa, NIH3T3 and SHYSY5Y cell lines that was not observed in 1,8-naphthalimides that lack an epoxide moiety. In particular, the compound (IX) was surprisingly found to initiate an irreversible s-phase arrest in HeLa, NIH3T3 and SHYSY5Y cell lines.

Active Compounds as Antifungal Agents

The active compounds of general formula (I) were also found to irreversibly arrest mitosis of fungi cells, thereby inhibiting the growth of the fungi cells. In particular, compound (IX) was surprisingly found to initiate an irreversible s-phase arrest in *Candida albicans*. Accordingly, the active compounds have antifungal activity and can be used as antifungal agents for inhibiting the growth of a fungus. It is therefore contemplated that the active compounds can be used as antifungal agents.

The inventors contemplate a method of inhibiting the growth of a fungus comprising exposing fungi cells to an effective amount of an active compounds. Exemplary fungal diseases include *Candida* (e.g. *Candida albicans*) and *aspergillus*.

One skilled in the art will recognize in light of the present disclosure that although the specified materials and conditions are important in practicing the invention, unspecified materials and conditions are not excluded as long as they do not prevent the benefits of the invention from being realized.

Screening Assay for Active Compounds

The applicant has demonstrated that IX can cause S-phase arrest in various cells including fungal and mammalian cells. It is envisaged that compounds structurally related to compound IX will exhibit similar activity and such compounds may be readily identified by the skilled person with the aid of the information described herein.

To confirm the ability of a compound to reduce the proliferation of a targeted cell various assays may be performed. In a preferred embodiment, the compound is tested to determine whether it can alleviate the reduction in cell growth (proliferation) induced by Cdc20 overexpression. Preferably, the Cdc20 overexpressor is a strain of *Saccharomyces cerevisiae*. Preferably, the yeast expresses multiple ($\geq 2$, more preferably $\geq 3, 4, 5, 6, 7, 8, 9$ or $10$) copies of Cdc20. In one embodiment the promoter may be an inducible promoter such as a Galactose inducible promoter. A suitable example of a yeast is US1392. Further details of the assay are set forth in the Examples section of this specification which includes a schematic representation of the assay. In one embodiment of the invention the assay conditions detailed in the Examples of this specification are followed to determine whether any particular compound is capable of inducing cell cycle arrest.

Other assays to investigate anti-proliferative activity may alternatively or additionally be used. See, for example, the assays described below in the Examples section. These methods include the measurement of DNA content (eg by FACS analysis) and cell division analyses (see FIGS. 2Aii, 2Aiii, 2Bii and 2Biii). Further, the skilled person will be able to devise further assays for testing compounds for their ability to induce cell cycle arrest.

In an eighth aspect of the invention there is provided a screening method, the method comprising: (a) providing a cell which overexpresses Cdc20 which overexpression causes a reduction in the proliferation of the cell; (b) exposing said cell to a candidate compound; and (c) determining whether said candidate compound alleviates the reduction in the proliferation of the cell.

The screening method may be used to identify compounds which exhibit antiproliferative activity. Such compounds may, for example, find utility in the treating of cancer patients.

In one embodiment the screening method may be used to identify compounds which are capable of inducing cell cycle arrest.

Preferably, the cell is a mammalian cell or a fungal cell. The fungal cell may, for example, be a yeast cell such as *Saccharomyces cerevisiae*.

The overexpression of Cdc20 may be conditional. For instance, expression of the Cdc20 gene may be under the control of an inducible promoter such as a galactose inducible promoter. In such a scenario, growth of the cell in a galactose-containing medium leads to overexpression of the Cdc20 gene and a reduction in cell growth is observed. The conditional yeast mutant strain US1392 may be used in the screening assay of the invention.

The person skilled in the art will readily be able to create Cdc20-overexpressors. Additionally, guidance may be gleaned from Lim and Surana (1996) *Mol. Gen. Genet.* 253: 138-148 (Cdc20, a β-transducin homologue, links RAD9-mediated G2/M checkpoint control to mitosis to *Saccharomyces cerevisiae*) which describes the creation of Cdc20 overexpressors which compromise the damage-induced checkpoint control.

The skilled person will readily be able to devise methods for determining whether a candidate compound results in an increase in the growth of the cell. For instance, growth of the cells may be measured spectrophotometrically (see for example FIG. 1).

Growth of cells treated with a candidate compound may be compared with the growth of cells which have not been treated with a candidate compound which may thereby serve as a control/point of comparison.

Biological Studies

In order to ascertain the functional role(s) and mechanism(s) of action of the compounds disclosed in the present invention, a number of biological studies were conducted. These are described in detail in the Examples below.

Yeast strains used in this study were haploid and congenic to the wild-type strain W303. Yeast mutants rad53-21 and chk1Δ were obtained from Dr. Yoli Sanchez and Dr. Wolfram Siede respectively. The *Candida albicans* strain was procured from Dr. Wang Yue (Institute of Molecular and Cell Biology, Singapore). A list of strains used is depicted in Table 1.

TABLE 1

| *Saccharoayces cerevisiae* STRAINS USED IN THIS STUDY | | |
|---|---|---|
| US155 | MATa rad9 Δ::URA3 ade2-1 can1-100 leu2-3 his3-11 trp1-1 | US LAB |
| US1234 | MATa pds1Δ::URA3 ade2-1 can1-100 leu2-3 his3-11 trp1-1 | US LAB |
| US1363 | MATa bar1Δ ade2-1 can1-100 leu2-3 his3-11 ura3 trp1-1 | US LAB |
| US1392 | MATa 6XGAL-Cdc20::TRP1 ade2-1 can1-100 leu2-3 his3-11 ura3 | US LAB |
| US3097 | MATa chk1 Δ::TRP1 ade2-1 can1-100 leu2-3 his3-11 ura3 | Wolfram Seide |
| US3138 | MATa bar1Δ mec1-1 ade2-1 can1-100 ura3 leu2-3 his3-11 trp1-1 | US LAB |
| US3196 | MATa rad53-21 ade2-1 can1-100 ura3 leu2-3 his3-11 trp1-1 | Y. Sanchez |
| US4900 | MATa bar1Δ RAD53-HA$_2$::URA3 ade2-1 can1-100 leu2-3 his3-11 trp1-1 | US LAB |
| US4901 | MATa bar1Δ mec1-1 RAD53-HA$_2$::URA3 ade2-1 can1-100 leu2-3 his3-11 trp1-1 | US LAB |

The organic compound library used to screen for compounds that could overcome the lethality induced by Cdc20 overexpression, was purchased from Chembridge Corporation, (San Diego, Calif., United States of America). The mammalian cell lines, HeLa and NIH3T3 were obtained from Dr. Cao XinMin (Institute of Molecular and Cell Biology, Singapore) and SHSY5Y was obtained from Dr. Tan Kuan Onn. The p53−/− mouse fibroblast knock out cell line was a kind gift from Dr. Kanaga Sabapathy (Institute of Molecular and Cell Biology, Singapore). Human Osteosarcoma cells, U2-OS, were obtained from Dr. Li Baojie (Institute of Molecular and Cell Biology, Singapore)

The Topoisomerase kit was purchased from Topogen Inc. (Columbus, Ohio, United States of America) and the mouse anti-α tubulin antibody used for staining mammalian cells was purchased from Sigma.

Fluorescently-conjugated anti-Rabbit Alexa Fluor 594 and anti-mouse Alexa Fluor 488 were purchased from Molecular probes. Antibodies against Cyclin E, Cyclin A, Cyclin B1, Chk1, Chk2, p53 were purchased from Santacruz Biotechnology Inc. (Santa Cruz, Calif., United States of America). Antibodies against Cyclin D1, phospho-Chk1 (Ser 317), phosphd-Chk2 (thr68), phospho-(Ser/Thr)ATM/ATR substrate, phospho-p53 (ser15) and phospho-Histone H3 (Ser10) were obtained from Cell Signaling. Anti-BrDU was procured from Amersham Pharmacia Biotechnology. Antibody against Actin was obtained from Abcam. Anti-PARP antibody was purchased from BD Pharmingen.

Yeast cells were routinely grown in yeast-extract peptone (YEP) or selective medium supplemented with 2% glucose (+Glu) or raffinose-galactose (Raff+Gal).

Standard molecular biology and molecular genetic techniques such as gene disruption, tetrad dissection, gene transplacement and PCR-based tagging of endogenous genes were used to construct plasmids and strains with various genotypes (shown in Table 1). Southern blot analysis or PCR-based genotyping were used routinely to confirm gene disruptions and gene transplacements. Therefore, the practice of the present invention will employ, unless otherwise indicated, conventional techniques of molecular biology, chemistry, biochemistry and recombinant DNA technology, which are well known to one of skill in the art. Such techniques are explained fully in the literature. See, for example, MOLECULAR CLONING: A LABORATORY MANUAL, $3^{rd}$ ed., Sambrook et al., Cold Spring Harbor Laboratory Press, Cold Spring Harbor, N.Y. (2001); DNA CLONING, vols. I and II, Glover, Ed. (1985); OLIGONUCLEOTIDE SYNTHESIS, Gait, Ed. (1984); NUCLEIC ACID HYBRIDIZATION, Hames and Higgins, Eds. (1984); and the series METHODS IN ENZYMOLOGY, Colowick and Kaplan, Eds., Academic Press, Inc., San Diego, Calif., USA.

Units, prefixes, and symbols may be denoted in their SI accepted form.

Identification of 2-methyl-1,8 epoxy Naphthalimide (Compound (IX)) from an Organic Compound Library The organic compound library consisting of 16,000 organic compounds from the Chembridge Diverset is a collection of diverse, pre-designed drug-like small molecules that were rationally selected based on 3D pharmacophore analysis. The library is formatted in 96 well microtitre plates to facilitate the screening process. Compounds dissolved in Dimethylsulphoxide (DMSO) at a concentration of 3 µM were incubated with US1392 and cell viability was measured using a microtitre-based assay. This is depicted schematically below:

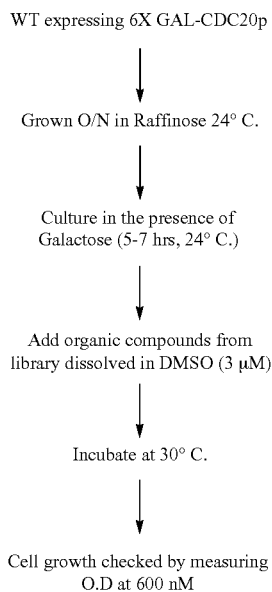

Organic compounds from the Diverset library were dissolved in DMSO at a final concentration of 3 µM and incubated with a yeast strain expressing six copies of Gal-CDC20 (US1392) in galactose. Cell viability was measured using a microtiter-based assay. Compounds that could counteract the lethality associated with Cdc20 overexpression were chosen for further characterization.

Only one organic compound allowed cell growth on Cdc20 overproduction and this compound was identified as 2-methylepoxy-1,8 naphthalamide (the Compound (IX)).

FIG. 1 depicts a graph plotting the survival of the US1392 yeast mutant strain treated with COMPOUND (IX) (black square-shaped data points). Treatment with dimethylsulfoxide (DMSO) served as the control (gray circle-shaped data points). Concentration was measured in optical density units (O.D. 600 nm) and cell survival/growth was measured over a period of several hours.

After a period of about 6 hours, cells treated with COMPOUND (IX) displayed exponential growth. In contrast, growth of cells treated with DMSO slowed down considerably.

In order to determine the physiological mechanism of action of COMPOUND (IX), its effect on wild-type (WT) Saccharomyces cerevisiae cells was tested. FIG. 2 depicts DNA content measurement and cell division analyses of wild-type yeast cells treated with COMPOUND (IX). Exponential cultures of wild-type (US1363) yeast cells were grown overnight in YEP+Glucose medium and diluted to an absorbance (O.D at 600 nm) of 0.3. Cells were treated with either 3 µM (FIG. 2B(i)) or 30 µM (FIG. 2A(i)) of COMPOUND (IX). Samples collected at indicated time points were utilised for measurement of DNA content by FACS analysis (FIGS. 2A(i) and 2B(i)) or for observing the mitotic spindle and state of nuclear division by direct immunofluorescence (FIGS. 2Aii, 2Aiii, 2Bii and 2Biii).

As shown in FIG. 2A(i) when treated with 30 µM COMPOUND (IX) the majority of cells displayed an early S-phase arrest. On the other hand, when treated with 3 µM COMPOUND (IX), the majority of cells displayed a late S-phase arrest. This can also be seen from the spindle staining, where late S-phase spindles (FIG. 2A ii) are better defined than the corresponding early S-phase spindles (FIG. 2B ii).

Next, wild-type (WT) yeast cells were treated with organic compounds that are structurally similar to COMPOUND (IX) to determine if these compounds were functionally similar to COMPOUND (IX). Exponential cultures of WT yeast cells were grown overnight in YEP+Glucose medium and diluted to an absorbance (O.D at 600 nm) of 0.3.

Figure 3A:
FIG. 3 depicts DNA distribution analysis of wild-type yeast cells treated with compounds that are similar to the active compounds and which do not exhibit antiproliferative activity.
Figure 3A:
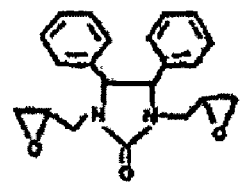
Figure 3A:
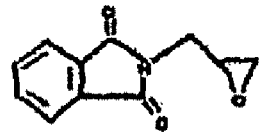
Figure 3B:
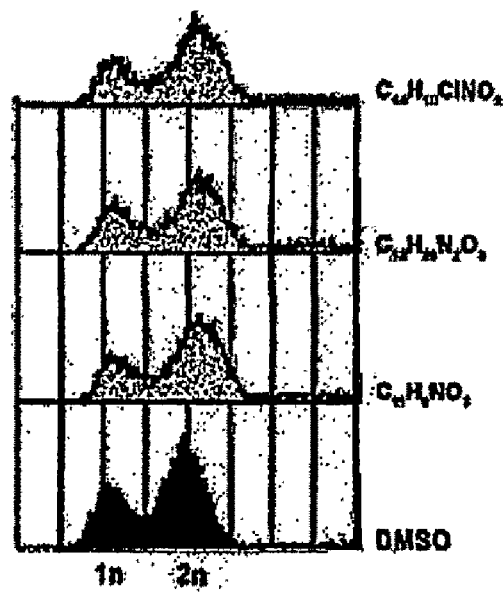

Organic compounds which were similar in structure to the active compounds were dissolved in DMSO and incubated with the cells for 4 hours. These compounds are shown in FIG. 3A. FIG. 3B shows DNA distribution analysis by flow cytometry of WT yeast cells treated with compounds of FIG. 3A. The effect of the compounds of FIG. 3A on the cell cycle was essentially identical to the effect of the control DMSO. Therefore, the compounds of FIG. 3A failed to induce S-phase arrest in the WT yeast cells.

Flow cytometry, Immunofluorescence and Visualization of Fluorescence Signals

To analyze DNA distribution of yeast cells by flow cytometry, cells were fixed overnight in 70% ethanol at 4° C., washed once with 0.2 M Tris-HCl (pH 7.5) containing 20 mM EDTA, and resuspended in the same buffer. Cells were then treated with RNase (1 mg/ml) for 4 h at 37° C., washed once with phosphate-buffered saline (PBS), re-suspended in 0.1 ml propidium iodide solution (50 µg/ml) and incubated overnight at 4° C. The cell suspension was diluted ten times with PBS and sonicated before performing flow cytometry. For measuring the DNA content of mammalian cells, cells were trypsinized, washed once with complete medium, resuspended in a solution containing 50 µg/ml propidium iodide and 200 µg/ml RNase. After incubation for 30 minutes at 37° C., cells were analyzed by flow cytometry. Cell Quest software was used for data analysis.

The method of Kilmartin and Adams [6], which is incorporated herein by reference) was used for immunofluorescence of yeast cells. For immunofluorescence of mammalian cells, tissue cultured cells were grown in coverslips, fixed with 3% paraformaldehyde and permeabilized with 0.25% Triton X-100. After blocking with 5% fetal bovine serum and 2% BSA, cells were incubated with primary antibody at room temperature for 2 hours followed by incubation with fluorescently conjugated secondary antibodies. To study BrDU incorporation, cells were fixed with 70% alcohol, treated with 2N HCl for 30 mins, neutralized with 0.1M Sodium Borate (pH:8.5) permeabilized with 0.25% TritonX-100, blocked with (5% FBS and 2% BSA) and incubated with anti-BrDU antibody. All fluorescence images were captured using a Leica DMRX microscope attached to a Hamamatsu charge-coupled device camera driven by Metamorph software (Universal Imaging Corporation).

Cell Extracts and Western Blot Analysis

Preparation of yeast crude extracts for western blot analysis and immunoprecipitation was carried out as described in Yeong et al [7]. Preparation of total cell lysates of mammalian cells was carried out by suspending the cells in RIPA buffer (50 mM Tris, pH-7.4, 150 mM NaCl, 1% NP-40, 1 mM EDTA, 0.1% SDS) in the presence of protease inhibitors, followed by centrifugation and clarification of the extracts at 13,000 rpm. Supernatants were used as the total cell extracts and used for Western blot analysis. The Enhanced chemiluminescence kit from Santa Cruz Biotechnology Inc., (Santa Cruz, Calif., United States of America) was used for all Western blot analyses according to the manufacturer's instructions.

Synchronization of Cells with a Factor Treatment and Activation of Replication Checkpoint by Compound (IX) Treatment For all experiments requiring synchronization of cultures at $G_1$, exponential phase cells were grown in medium at 24° C. containing either 1 µg/ml α factor for bar1Δ cells, or 5 µg/ml for BAR1 cells. After 2.5 to 3.0 hours of treatment, cells were filtered, washed and re-suspended in fresh medium pre-incubated at the appropriate temperature. For experiments where treatment with COMPOUND (IX) was required, either cells synchronized in G1 with α factor treatment were released into medium containing COMPOUND (IX), or overnight grown exponential phase cultures were treated with different concentrations as indicated in the individual experiments. For determining cell viability, cells collected at various time points were counted, 200 cells were plated in YEP+glucose plates incubated at 24° C. and the number of colonies was counted after 5 days.

Next DNA binding assays were performed to further understand the S-phase arrest-inducing properties displayed by COMPOUND (IX). The method of Dunstan et al [5] was used to test the ability of the Compound (IX) to bind DNA. Briefly, various concentrations of the Compound (IX) were incubated with a constant amount of plasmid DNA for 30 minutes at 37° C. in topoisomerase I drug kit buffer (Topogen Inc., Columbus, Ohio, U.S.A).

After incubation, the samples were separated by agarose gel electrophoresis (1% agarose) and later visualized by staining the gel with ethidium bromide. Binding of the compound to DNA was indicated by retardation of the mobility of DNA on the gel.

FIG. 4A depicts the band-shift assay. Slower-migrating retarding forms of the DNA-COMPOUND (IX) complexes were observed using agarose gel electrophoresis.

It was observed that COMPOUND (IX) bound DNA in a concentration-dependent manner. Plasmid DNA incubated with 100 µM of COMPOUND (IX) migrated slower than plasmid DNA incubated with 10 µM or 50 µM of COMPOUND (IX).

FIG. 4B depicts induction of RAD53 phosphorylation in a MEC1 dependent manner. RAD53, a protein kinase, has been shown to be required for DNA damage-induced checkpoint arrest in G1, SM, and G2/M in mitosis. Mec1p and Tel1p regulate rad53p phosphorylation.

WT (US4909) and mec1-1 (US4901; a kinase-deficient strain) yeast cells expressing RAD53-$HA_2$ were arrested with α factor and released into 30 µM of COMPOUND (IX). Samples collected at indicated time points (180 minutes and 240 minutes) were electrophoresed on 10% SDS-PAGE gels and Western-blotted. The blots were probed with anti-$HA_2$ antibody to detect the migration of RAD53-$HA_2$ after treatment with COMPOUND (IX). (*) indicates the position of the phosphorylated forms of Rad53. As shown in the figures, RAD53 was phosphorylated only in the WT controls and not in the mec1-1 mutant. Therefore, COMPOUND (IX) induces RAD53 phosphorylation in a MEC1 dependent manner. This is suggestive of the activation of the replication checkpoint mechanism.

Figure 6A:
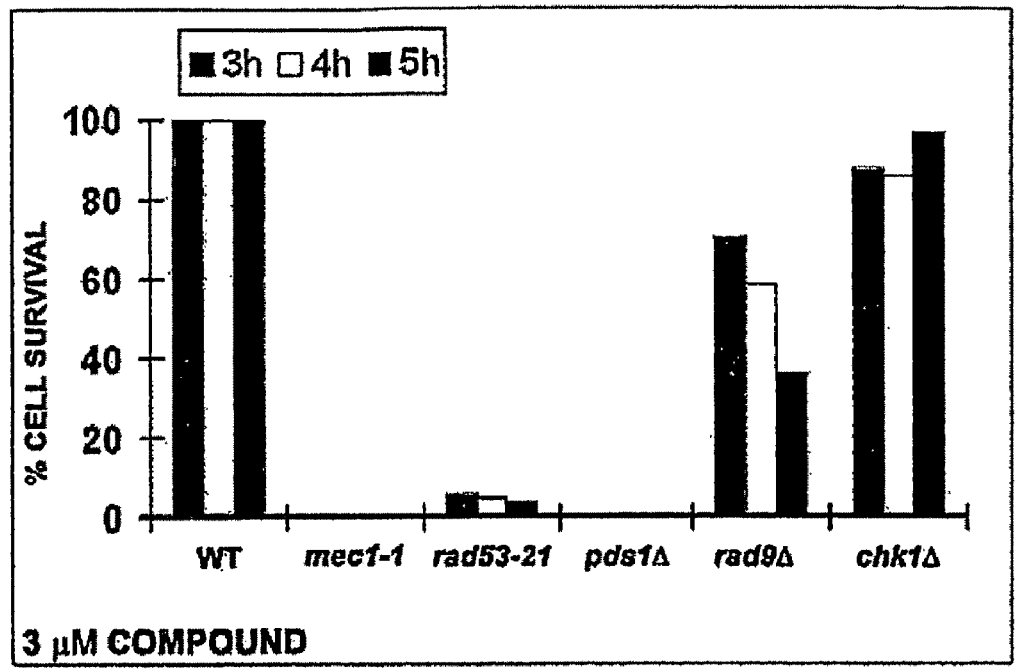
FIG. 6 depicts survival of wild-type and replication checkpoint-defective cells treated with the Compound (IX).
Figure 6B:
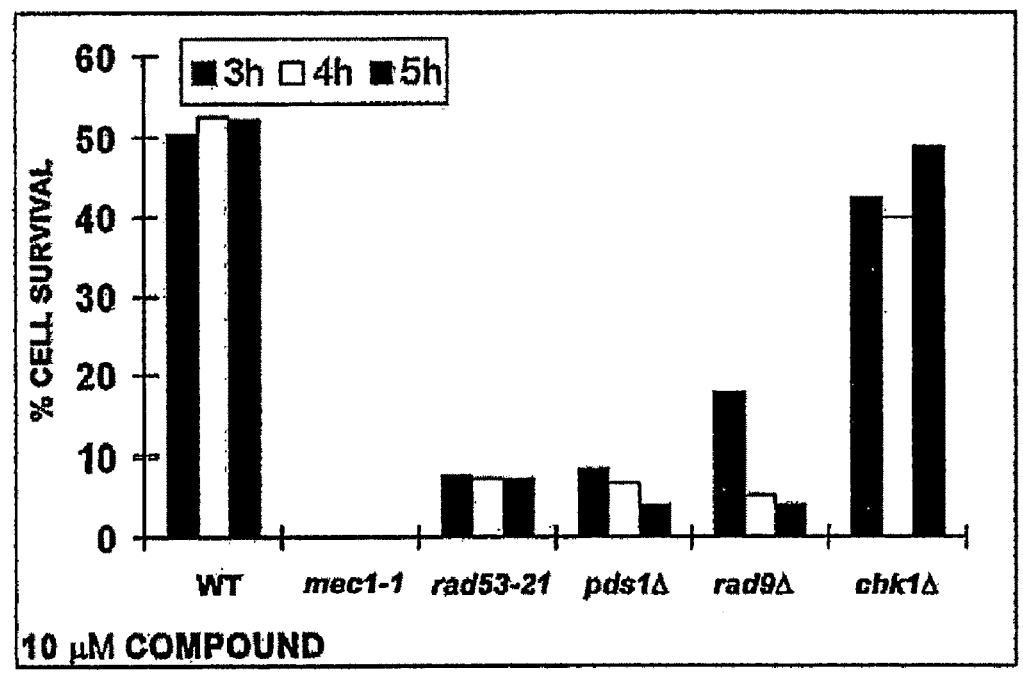

FIGS. 5 and 6 demonstrate that replication checkpoint deficient yeast mutant cells display significant lethality as compared to wild-type cells. FIG. 5 depicts cell division and growth of WT and mec1-1 cells treated with the COMPOUND (IX). Exponential phase cultures of WT (US1363) and mec1-1 (US3138) cells were treated either with 3 µM or 30 µM of COMPOUND (IX). Samples collected at indicated time points were processed for flow cytometric analysis of DNA content and for observing the status of nuclear division and mitotic spindles by immunofluorescence.

FIGS. 5A and 5B depict that mec1-1 cells treated with COMPOUND (IX) show elongated spindles and nuclear division. In FIGS. 5c and 5d, aliquots collected from the above-mentioned experiments were washed thoroughly with phosphate-buffered saline and cells were counted using a hemocytometer.

500 cells were spread on YEP+Glucose plates and incubated at 24° C. for five days and colonies were counted after five days. These figures show that the mec1-1 mutant cells (replication checkpoint deficient strains) display significant lethality as compared to WT cells, although higher concentrations of COMPOUND (IX) (30 µM) induced some loss of viability in WT cells as well.

FIG. 6 also shows that replication checkpoint mutants exhibit sensitivity to COMPOUND (IX). Exponential cultures of WT (US1363), mec1-1 (US3138), rad53-21 (US3196), pds1Δ (US1234), rad9Δ US155) and chk1Δ (US3097) cells were treated with either 3 µM or 10 µM of COMPOUND (IX) and aliquots of cells withdrawn at indicated time points were washed, counted and equal numbers were plated on YEP+Glucose plates. Colonies observed after five days were counted and percentage cell survival was calculated and represented graphically. While the replication deficient mutants (mec1-1, rad53-21 and pds1Δ displayed significant lethality as compared to WT cells, the DNA damage checkpoint deficient mutants (rad9Δ and chk1Δ were comparatively less sensitive to the addition of COMPOUND (IX). This reinforces previous results which indicated that COMPOUND (IX) activates the replication checkpoint.

Treatment of Mammalian Cells with Compound (IX)

Mammalian cell lines HeLa, NIH3T3 (human cervical cancer cell line) and SH5S5Y (metastatic neuroblastoma cell line) were routinely cultured in Complete Dulbecco's Modified Eagle's Medium (DMEM). Complete medium was made by supplementing DMEM (pH: 7.4) with 0.03% glutamine, antibiotic-antimycotic solution, (10 Units/ml of Penicillin G-Sodium, 10.00 µg/ml of Streptomycin sulphate, and 25 µg/ml of Amphotericin B) and 10% fetal bovine serum. Five ml of cell suspension ($1 \times 10^5$ cells/ml) in complete medium was plated in a 25-cm$^2$ tissue culture flask. The culture dishes were incubated under a humidified atmosphere containing 5% $CO_2$ and 95% air at 37° C. Cell viability was determined using Trypan blue dye-exclusion test. It was ensured that the cells were at least 95% viable for all experiments.

Mammalian cell lines were routinely maintained as described above. Exponentially growing cells were treated with COMPOUND (IX) which was dissolved in DMSO and samples were collected for FACS analysis to measure DNA content. The compound was added at a final concentration of 5 µM or 6.5 µM to activate the replication checkpoint in mammalian cells and incubated for 24 hours for most cell lines unless mentioned otherwise in the figure legends. It was observed that at higher concentrations (10-20 µM) the compound caused apoptosis as measured by FACS analysis and cleavage of the protein PARP.

It was generally observed that at higher concentrations the compound was toxic thus leading to cell death and apoptosis as measured by trypan blue staining.

Measurement of Cell Proliferation Using MTS Assay

Cultures of mammalian cells were grown on 96-well plates in 100 µl of Complete medium and incubated with either DMSO or with various concentrations of Compound (IX) and incubated at 37° C. for either 24, 48 or 72 hours. At the end of the incubation period, 20 µl of CellTiter Aqueous one solution reagent containing the MTS tetrazolium compound (Promega) was added and the cells were incubated for 150 mins. The absorbance was then recorded at 490 nM with a 96-well reader.

Figure 7A:
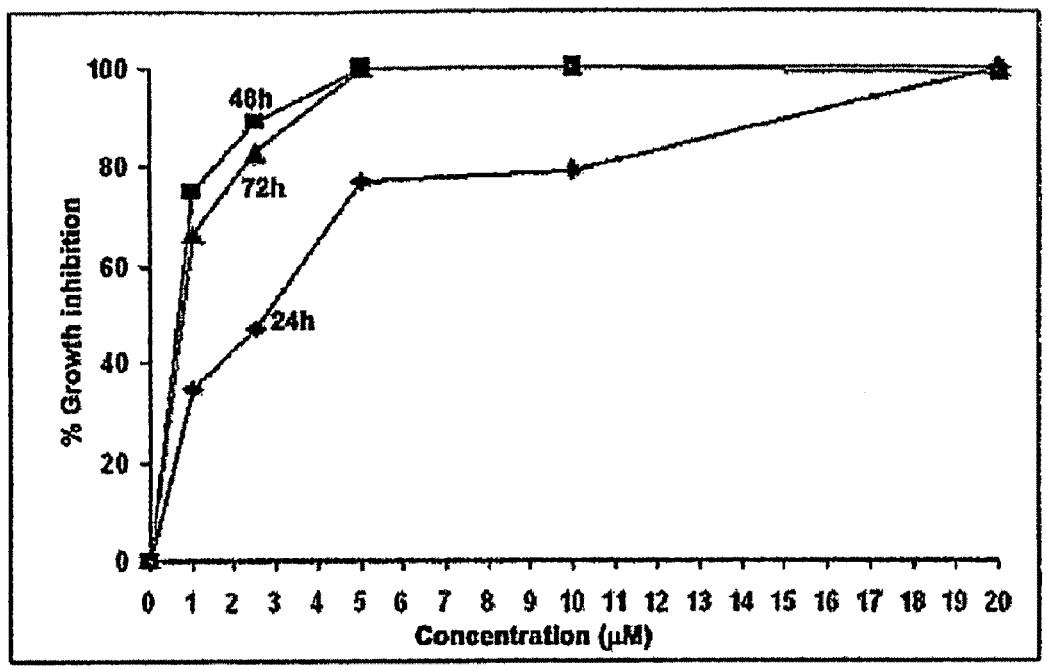
FIG. 7 depicts growth characteristics and cell division of HeLa cells treated with the Compound (IX).
Figure 7B:
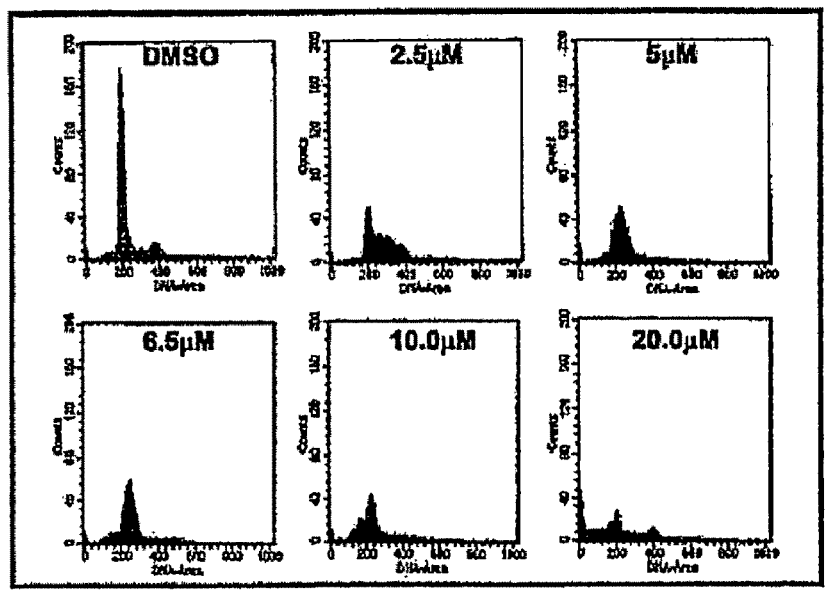
Figure 7C:
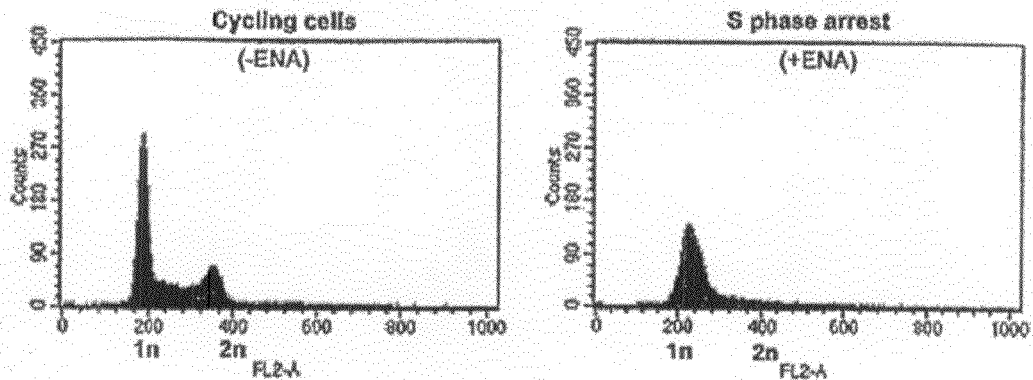
Figure 7D:
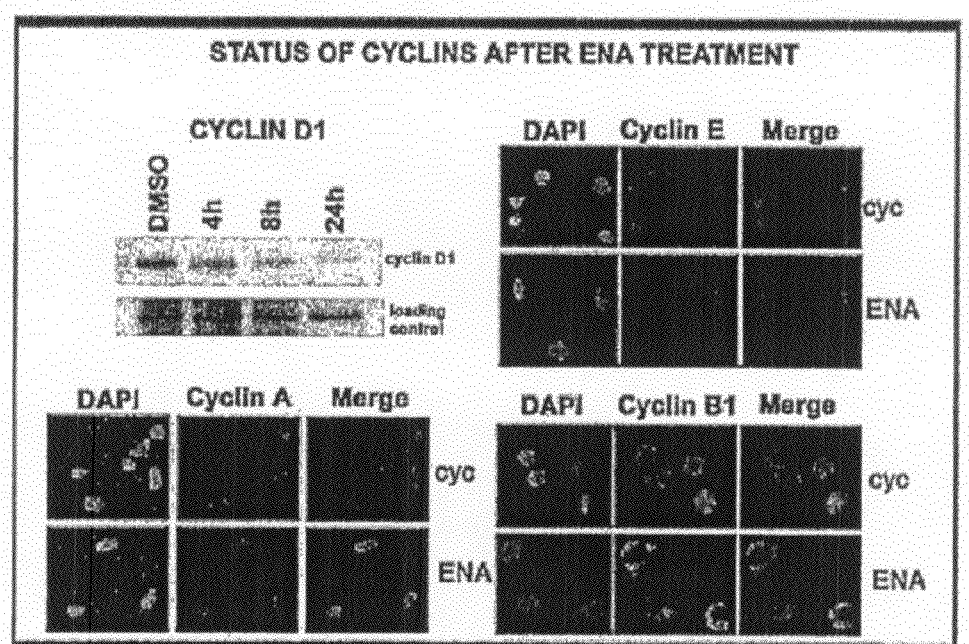
Figure 7E:
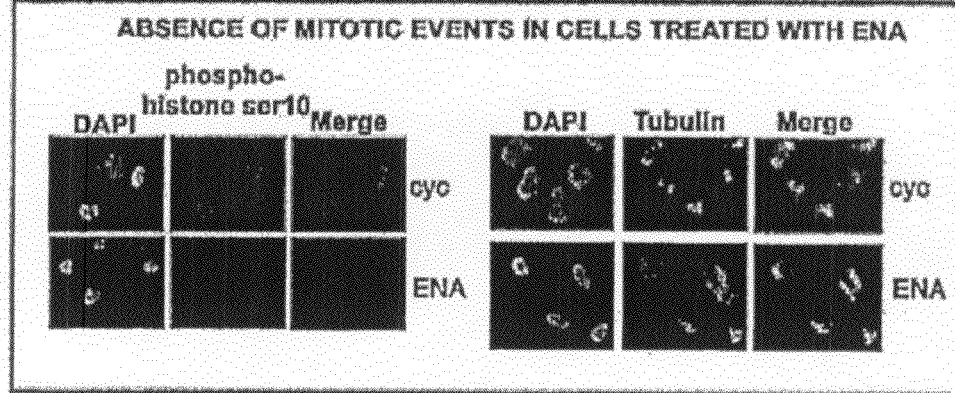
Figure 8B:
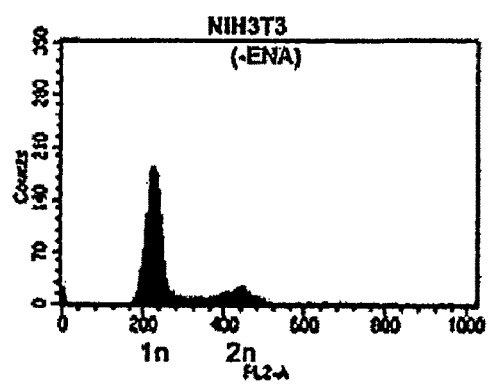
FIG. 8 depicts the effects of treating immortalized and metastatic cancer cell lines with the Compound (IX).
Figure 8B:
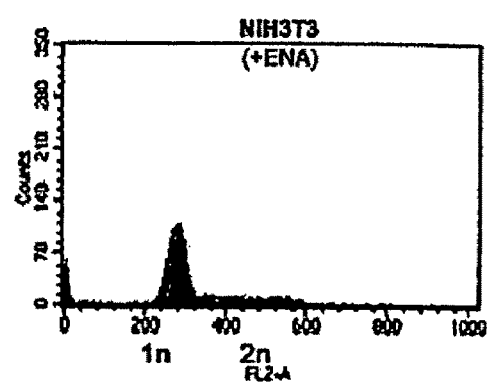
Figure 8B:
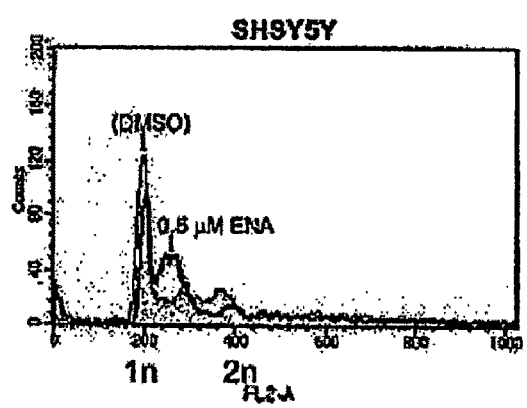

FIGS. 7 and 8 show that the mammalian cell lines indicated above undergo an irreversible cell cycle arrest in the S phase of the cell cycle when treated with COMPOUND (IX).

In FIG. 7A, HeLa cells were treated with various concentrations of Compound (IX) (1, 2.5, 5.0, 6.5, 10.0 and 20.0 µM for 24, 48 or 72 hours respectively). After incubation with the compound, cells were incubated for 2 hours with MTS reagent and absorbance was recorded at 490 with a 96-well reader. AS a control, HeLa cells were treated under identical conditions with DMSO. Percentage growth inhibition was calculated by comparing the readings between Compound (IX)-treated and DMSO-treated samples. As shown in the graph, percentage growth inhibition was higher for samples treated for 48 hours and 72 hours. Growth inhibition was also concentration-dependent, but seemed to plateau at concentrations higher than 6 µM.

In FIG. 7B, HeLa cells were treated with Compound (IX) for 24 hours and samples were collected for FACS analysis to measure DNA content. It can be seen that S-phase arrest is induced at concentrations of about 5-6.5 µM, while at higher concentrations (10-20 µM, cells undergo apoptosis).

In FIG. 7, exponentially growing HeLa cultures were either mock treated with DMSO or with 6.5 µM of COMPOUND (IX) dissolved in DMSO, incubated for 24 hours and samples were collected and analyzed by flow cytometry (for measurement of DNA content, as in FIG. 7C) or Western Blotting (as in FIG. 7D, first panel) or by staining with antibodies against cyclins and other mitotic markers (as in FIG. 7D, remaining panels and FIG. 7E).

As seen in the second panel of FIG. 7C, addition of COMPOUND (IX) induces S-phase arrest. Also, levels of the Cyclin D1 protein decreased upon treatment with COMPOUND (IX) as can be seen in the first panel of FIG. 7D.

FIG. 7E shows HeLa cells that were grown on coverslips, treated with COMPOUND (IX) as described above, and stained for mitotic spindles by indirect immunofluorescence. While metaphase, anaphase and telophase type of mitotic spindles could be observed in the mock treated cultures, only interphase tubulin arrays (right-hand panel) were seen in the cells treated with COMPOUND (IX), suggesting an S phase arrest. This is also observed in the left-hand panel in which cells were stained with antibodies against phospho-histone ser10, another mitotic marker.

Similarly, in FIG. 8, it was observed that COMPOUND (IX) arrests immortalized cell lines (NIH3T3) and metastatic cancer cell lines (SHYSY5Y) in the S phase of the cell cycle. In FIG. 8A, logarithmic phase NIH3T3 cells were treated with 5.0 µM of COMPOUND (IX) for 30 hours and samples collected after 30 hours were analysed for measurement of DNA content by FACS analysis. As shown in the right-hand panel, addition of COMPOUND (IX) to the NIH3T3 cells induces an S phase arrest while NIH3T3 cells not treated with COMPOUND (IX) complete S phase. In FIG. 8B, exponential phase SHYSY5 (human neuroblastoma) cells were treated with 0.5 µM of COMPOUND (IX) for 30 hours and a sample collected at the end of the experiment was analyzed by flow cytometry for DNA content measurement. Compared to treatment with DMSO (control), treatment with COMPOUND (IX) caused the majority of the cells to arrest with less than two copies of their DNA synthesized. Furthermore, this effect was achieved with concentrations as low as 0.5 µM COMPOUND (IX).

To further investigate possible mechanisms and molecules playing a part in the S-phase arrest observed in the examples described above, dependency of the S phase arrest on p53 status was investigated. P53 is a well-characterized tumor suppressor and several cancers frequently show mutations in the p53 gene and/or its regulators.

Figure 9:
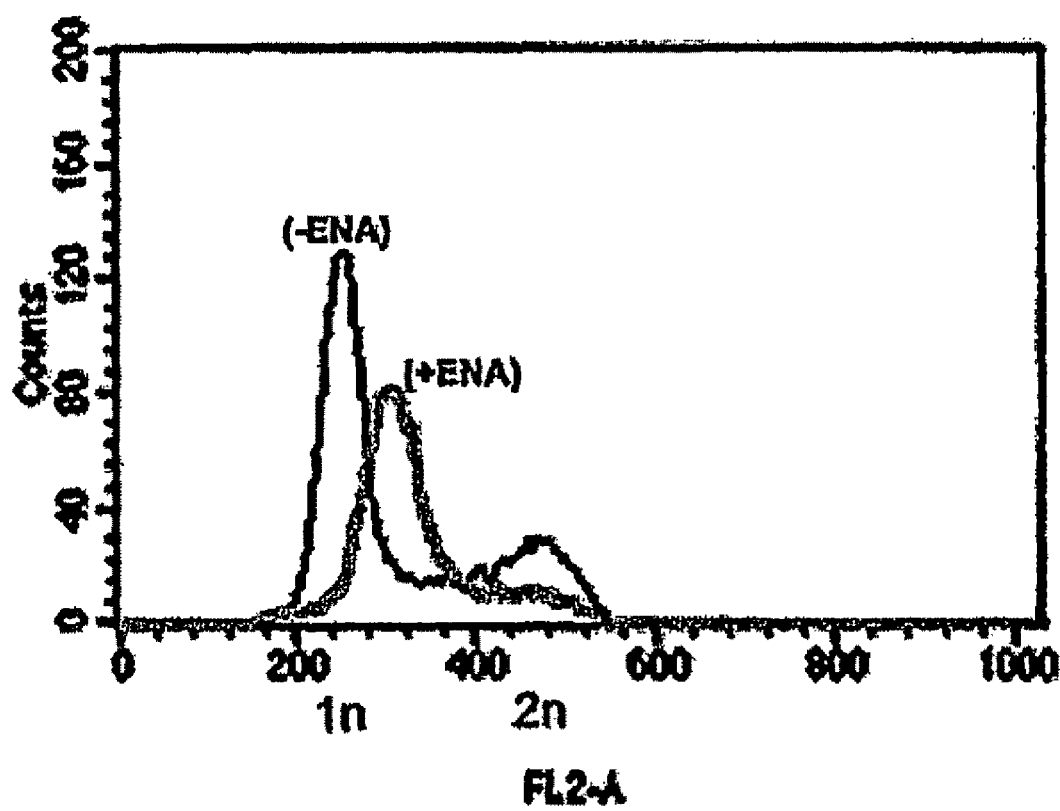
FIG. 9 depicts the effect of treating mouse p53−/− knock-out cell lines with the Compound (IX).

Mouse p53−/− knockout cell lines (lacking a functional p53 gene) were cultured and exponential phase cells were treated with 51M of COMPOUND (IX). Thirty hours later, cells were collected for analysis of DNA content by flow cytometry. FIG. 9 depicts the results. Treatment with COMPOUND (IX) successfully induced an S phase arrest in the p53−/− knockout cell lines thereby demonstrating that cell cycle arrest in the S phase appears not to require an intact p53.

Since COMPOUND (IX) was a potent inducer of S phase arrest, its effect on a pathogenic fungus was tested. Exponential phase cultures of *Candida albicans* strain were diluted to an O.D of 0.3 and treated with either DMSO or 30M of compound (IX). Absorbance of aliquots withdrawn at 60-minute intervals was measured to plot cell viability. As depicted in FIG. 10(A), while the O.D of control DMSO treated cells increased with time, that of the COMPOUND (IX) treated cultures stabilized at the starting value. In FIG. 10(B), overnight grown *Candida albicans* cultures were counted and 400 cells were plated on YEP+Glucose+COMPOUND(IX) (30 µM). Plates containing YEP+DMSO were used as control plates. Plates were incubated at 24° C. and photographed after 5 days. As shown on the right-hand panel, *C. albicans* cells show a striking loss of viability when treated with COMPOUND (IX). Therefore COMPOUND (IX) can act as a potent antifungal agent for diseases in humans, animals and plants.

Effect of Compound (IX) on the ATM/ATR Pathway

The Chk2 tumor suppressor protein and the checkpoint protein kinase ATM (ataxia-telangiectasia-mutated) are required for correct operation of both the G1 and G2 damage checkpoints. ATM is necessary for phosphorylation and activation of Chk2 in vivo and can phosphorylate Chk2 in vitro [8], [9] and [10].

Like ATM, ATR (ataxia telangiectasia and Rad3 related) serves as a checkpoint kinase that halts cell cycle progression and induces DNA repair when DNA is damaged. Loss of ATR results in a loss of checkpoint control in response to DNA damage, leading to cell death, and deletion of the ATR gene in mice is embryonic lethal [11].

The present inventors therefore sought to investigate whether Compound (IX) acted through the ATM/ATR pathway.

Figure 11A:
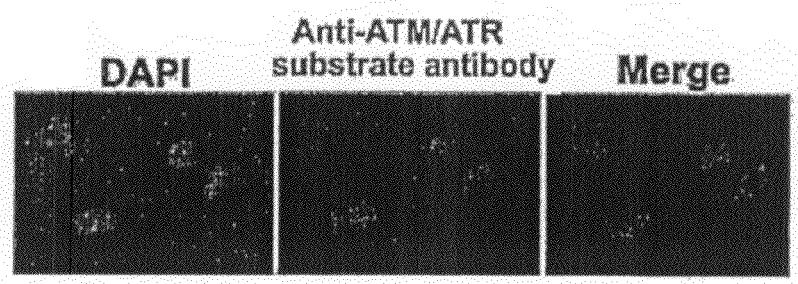
FIG. 11 depicts the effects of the Compound (IX) on the ATM/ATR pathway and the CHK genes in HeLa cells.

FIG. 11 shows the effect of Compound (IX) on the ATM/ATR pathway. In FIG. 11A, HeLa cells treated with 6.5 µM COMPOUND (IX) were collected 24 hours later for immunofluorescence and stained with Anti ATM/ATR substrate antibody. It can be seen from the antibody staining that COMPOUND (IX) activates the ATM/ATR pathway in HeLa cells and by corollary, other mammalian cells.

Figure 11B:
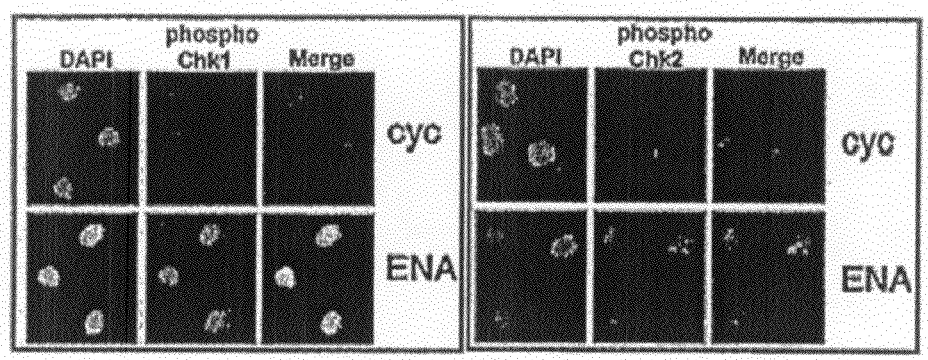
Figure 11C:
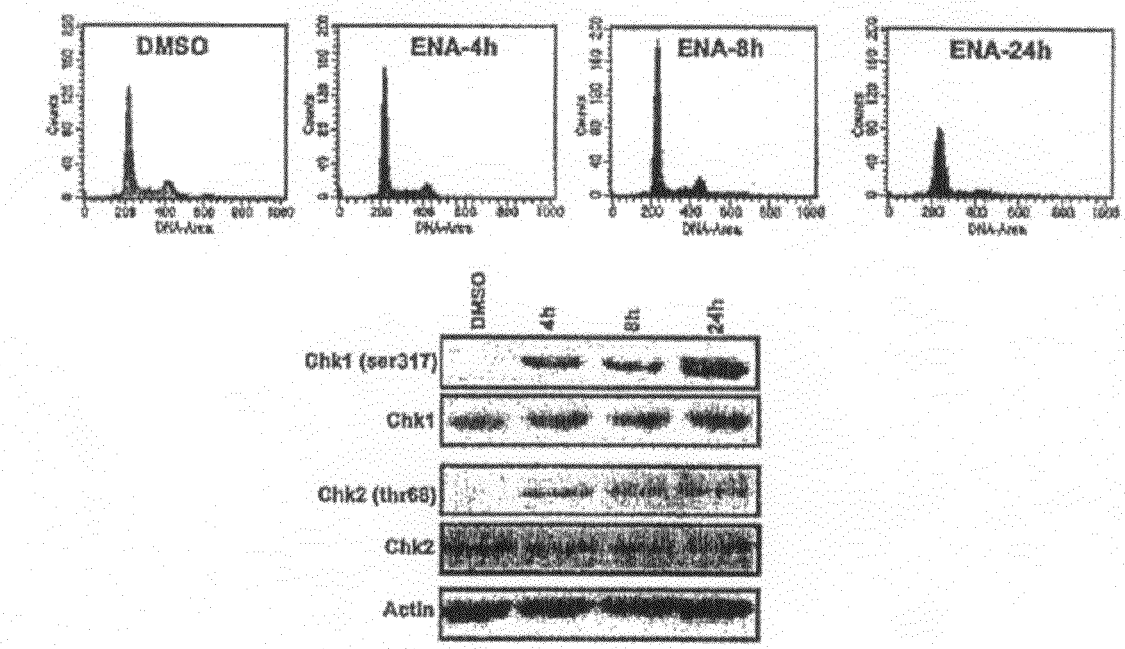

In FIG. 11B, HeLA cells were either treated with DMSO as control or with 6.5 µM COMPOUND (IX) and 24 hours later, cells were fixed and stained with anti-phospho Chk1 (ser317) or anti-phbspho Chk2 (thr68). In FIG. 11C, cells were treated with DMSO as control or with 6.5 µM COMPOUND (IX) and 24 hours later, cells were fixed and stained with anti-phospho Chk1 (ser317) or anti-phospho Chk2 (thr68). Samples collected at indicated points were analysed by Western blotting. Actin was used as the loading control.

In both FIGS. 11B and 11C, it can be seen that CHK1 and CHK2 are phosphorylated in response to treatment with COMPOUND (IX). These results are in conformance with studies demonstrating that ATM is necessary for phosphorylation and activation of Chk2 in vivo and can phosphorylate Chk2 in vitro, as described earlier.

Effect of Compound (IX) on the Apoptosis Pathway in Mammalian Cells

Figure 12A:
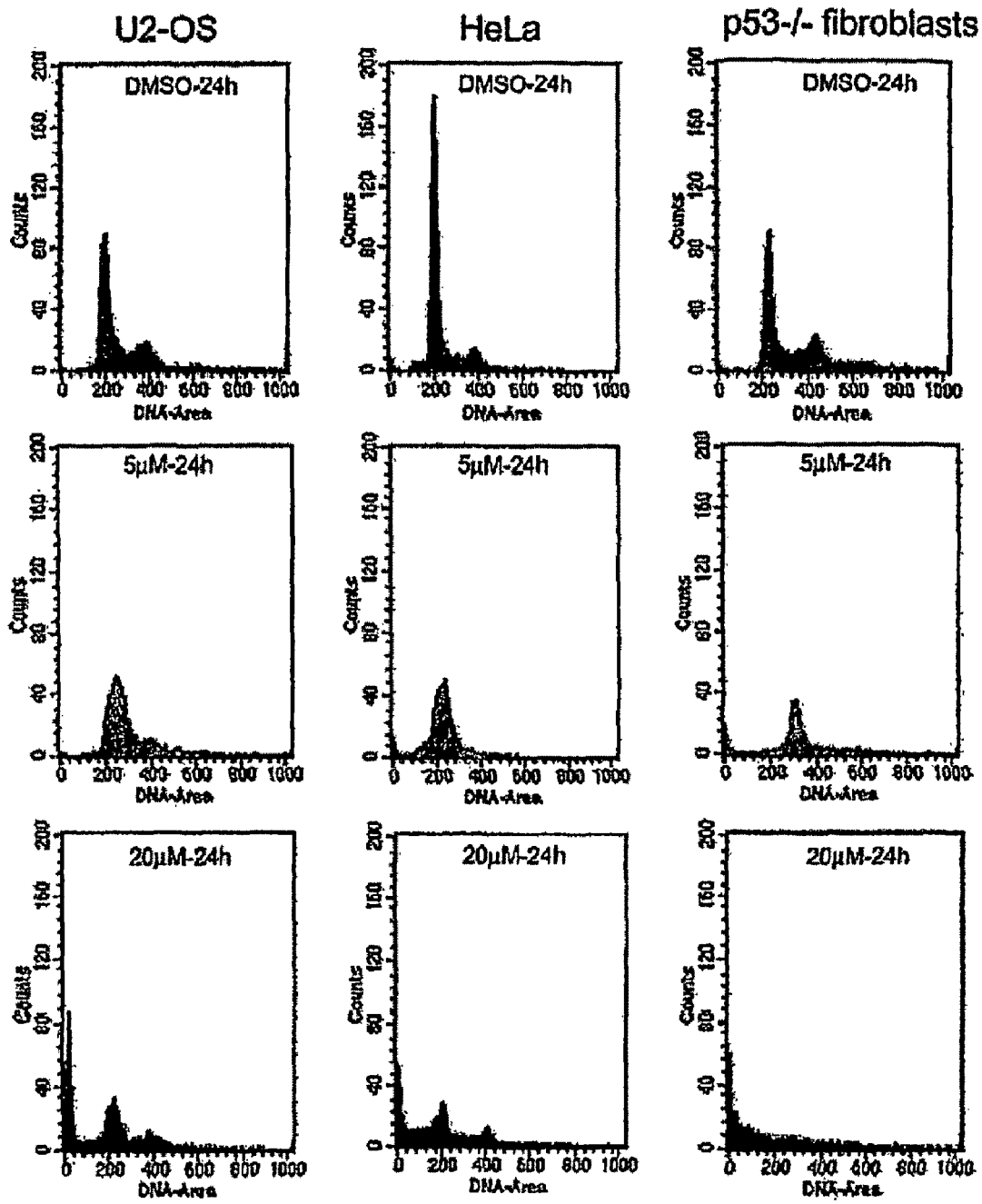
FIG. 12 depicts the apoptotic effects of the Compound (IX) on HeLa, U2-OS and p53−/− cells treated with the Compound (IX).
Figure 12B:
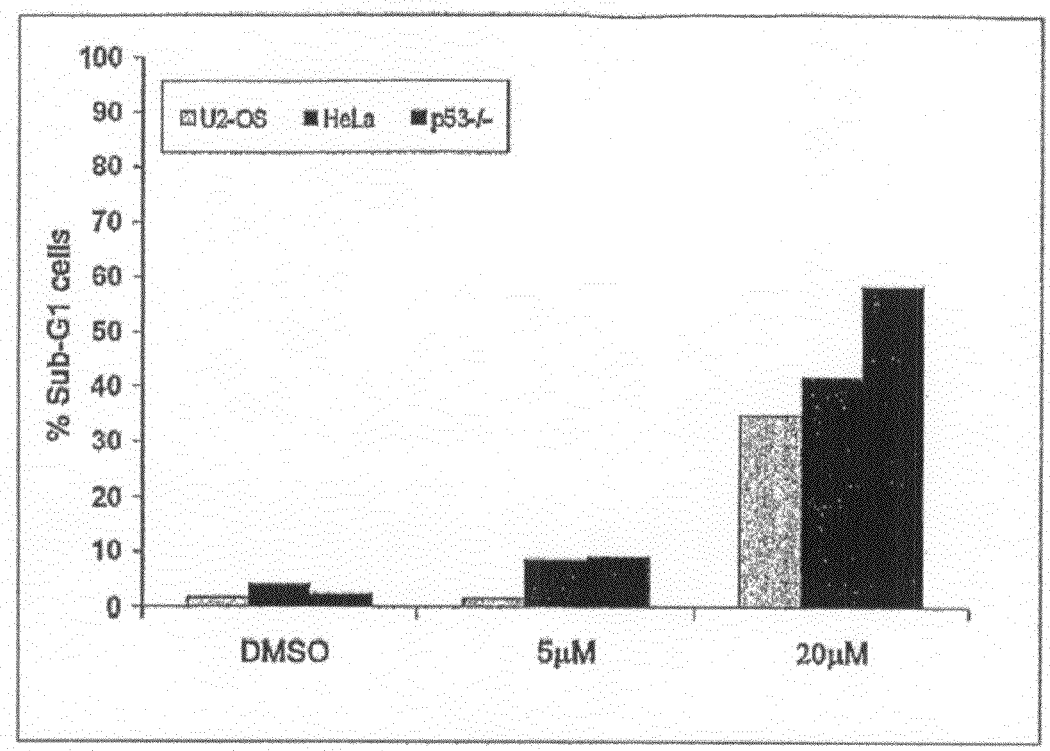
Figure 12C:
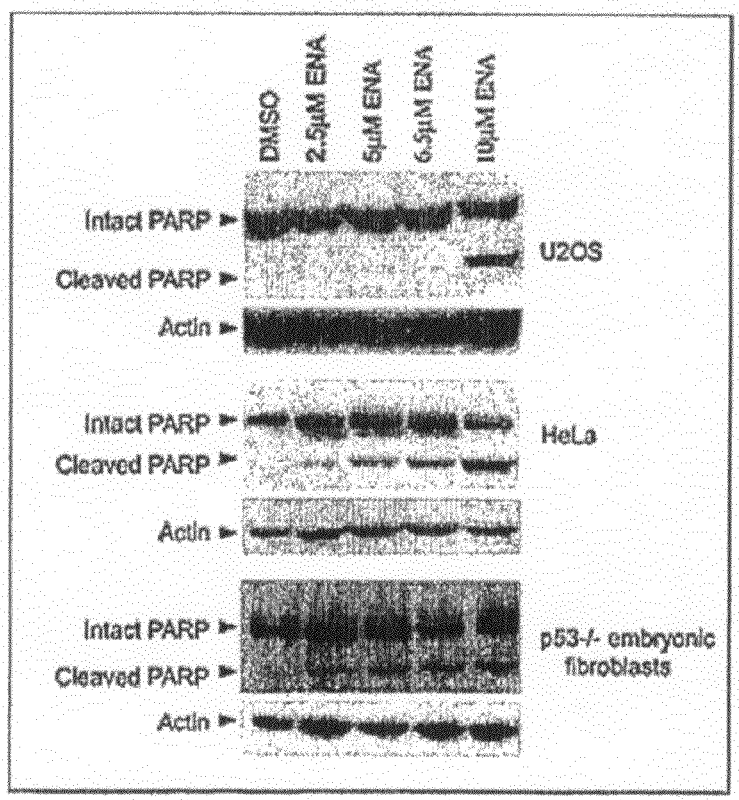

HeLa, U2-OS and p53-/- mouse embryonic fibroblast cells were cultured and treated with 51M or 20 µM COMPOUND (IX) for 24 hours and later fixed and stained with propidium iodide. FACS analysis was performed to quantitate the percentage of cells with sub-G1 DNA content as shown in FIGS. 12(A) and 12(B) as a late indicator of apoptosis. In FIG. 12(C), cells were treated with and samples were analyzed for cleavage of intact PARP into the 85 kDA subunit as an indicator of apoptosis.

PARP (Poly (ADP-ribose) polymerase [NAD+ADP-ribosyltransferase; NAD+:poly adenosine-diphosphate-D-ribosyl)-acceptor ADP-D-ribosyltransferase, EC 2.3.2.30] is a highly conserved nuclear enzyme present in higher eukaryotes. The enzyme is a $Zn^{2+}$ dependent DNA binding protein that recognizes DNA strand breaks and is implicated in DNA repair and in the apoptotic response of cells. As a marker for apoptosis, PARP cleavage has been variably shown to occur early in the response as a result of the activity of CPP32 (caspase-3, CASP3). PARP cleavage correlates well with chromatin condensation and has been shown to be associated with the condensed chromatin in apoptotic cells, as a measure of apoptosis appearing as early as 3 hours post apoptosis inducing event, and precedes the ability to detect actual DNA fragmentation.

A gradual cleavage of intact PARP on treatment with increasing concentrations of COMPOUND (IX) was observed. It was also observed that COMPOUND IX induces apoptosis at higher concentrations independent of functional p53.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

REFERENCES

1. Hartwell, L. H., and Weinert, T. A. (1989). Checkpoints: controls that ensure the order of cell cycle events. Science 246, 629-634.
2. Melo J. and Toczyski, D. (2002). A unified view of the DNA damage checkpoint. Curr. Opin. Cell Biol. 14, 237-245.
3. Longhese, M. P., Clerici, M., and Lucchini, G. (2003) The S-phase checkpoint and its regulation in Saccharomyces cerevisiae. Mutat Res. 532, 41-58.
4. Clarke, D. J., Segal, M., Jensen, S., and Reed, S. I. (2003). Mec1p regulates Pds1p levels in S phase: complex coordination of DNA replication and mitosis. Nat Cell Biol. 3, 619-627.
5. Dunstan, H. M., Ludlow, C., Goehle, S., Cronk, M., Szankasi, P., Evans, D. R. H., Simon, J. A., and Lamb J. R. (2002). Cell-based assays for identification of novel double-strand break-inducing agents. J. Natl. Cancer Institute. 94.88-94.
6. Kilmartin, J. V., and Adams, A. E. (1894). Structural rearrangements of tubulin, and actin during the cell cycle of the yeast Saccharomyces. J. Cell Biol. 98. 922-33.
7. Yeong, F. M., Lim, H. H., Padmashree, C. G., and Surana, U. (2000). Exit from mitosis in budding yeast: biphasic inactivation of the Cdc28-Clb2 mitotic kinase and the role of Cdc20. Mol. Cell. 5, 501-511.
8. Xu, J., Xin, S, and Du, W. et al. (2001). *Drosophila* Chk2 is required for DNA damage-mediated cell cycle arrest and apoptosis. FEBS Lett. 508(3): 394-8.
9. Abdu, U., Brodsky, M. and Schüpbach, T. (2002). Activation of a meiotic checkpoint during *drosophila* oogenesis regulates the translation of Gurken through Chk2/Mnk. Cur. Bio. 12: 1645-1651.
10. Masrouha, N., Yang, L., Hijal, S. Larochelle, S, and Suter, B. (2003). The *Drosophila* chk2 gene loki is essential for embryonic DNA double-strand-break checkpoints induced in s phase or G2. Genetics 163(3): 973-982.
11. Cortez D, Guntuku S, Qin J, Elledge S J. ATR and ATRIP: partners in checkpoint signaling. Science. 2001 Nov. 23; 294(5547): 1713-6.

The invention claimed is:

1. A method of reducing the proliferation of a targeted cell, wherein the cell is a cell of a cancer selected from cervical cancer, metastatic neuroblastoma and osteosarcoma, the method comprising exposing the cell to an effective amount of a compound of general formula (I):

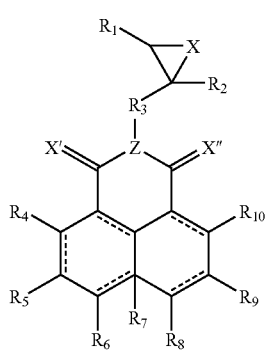

(I)

and the pharmaceutically acceptable salts, individual isomers and mixtures of isomers thereof, wherein X, X' and X" are independently O or S;

Z is N;

R$_3$ is optional and is selected from the group consisting of optionally substituted C$_{1-8}$ alkylene optionally substituted C$_{2-6}$ alkenylene, and optionally substituted C$_{2-6}$ alkynylene;

R$_1$, R$_2$, R$_4$, R$_5$, R$_6$, R$_7$, R$_8$, R$_9$, and R$_{10}$ are independently selected from the group consisting of hydrogen, optionally substituted C$_{1-8}$ alkyl, optionally substituted C$_{2-6}$ alkenyl, optionally substituted C$_{2-6}$ alkynyl, optionally substituted C$_{1-6}$ alkoxy, optionally C$_{1-6}$ thioalkyl, optionally substituted C$_{5-10}$ aryl, optionally substituted C$_{6-11}$ alkylaryl, optionally substituted C$_{1-6}$ alkylamino, optionally C$_{1-6}$ alkylcarbonyl, optionally substituted C$_{1-6}$ alkylsulfonamino, optionally substituted (C$_1$-C$_6$) alkylsulfinyl, optionally substituted C$_{1-6}$ alkylcarbonylamino, optionally substituted hetero(C$_4$-C$_{10}$) aryl, hydroxyl, halogen, cyano, nitro, amino, formyl, and thiol; and

- - - indicates an optional double bond.

2. A method as claimed in claim 1, wherein the exposing is performed in vitro or in vivo.

3. A method according to claim 1, wherein X, X' and X" are independently O or S.

4. A method according to claim 1, wherein X, X' and X" are O.

5. A method according to claim 1, wherein R$_1$, R$_2$, R$_4$, R$_5$, R$_6$, R$_7$, R$_8$, R$_9$, and R$_{10}$ are independently selected from the group consisting of optionally substituted C$_{1-8}$ alkyl, optionally substituted C$_{2-6}$ alkenyl, optionally substituted C$_{2-8}$ alkynyl, optionally substituted C$_{1-4}$ alkoxy, optionally substituted C$_{1-4}$ thioalkyl, optionally substituted C$_{6-8}$ aryl, optionally substituted C$_{7-9}$ alkylaryl, optionally substituted C$_{1-4}$ alkylamino, optionally substituted C$_{1-4}$ alkylcarbonyl, optionally substituted C$_{1-4}$ alkylsulfonamino, (C$_1$-C$_6$) alkylsulfinyl, optionally substituted C$_{1-4}$ alkylcarbonylamino, and optionally substituted hetero (C$_4$-C$_8$) aryl.

6. A method according to claim 1, wherein R$_1$, R$_2$, R$_4$, R$_5$, R$_6$, R$_7$, R$_8$, R$_9$, and R$_{10}$ are independently selected from the group consisting of optionally substituted C$_{1-6}$ alkyl, optionally substituted C$_{2-6}$ alkenyl, optionally substituted C$_{2-6}$ alkynyl, optionally substituted C$_{1-2}$ alkoxy, optionally substituted C$_{1-2}$ thioalkyl, optionally substituted C$_{6-7}$ aryl, optionally substituted C$_{1-2}$ alkylamino, optionally substituted C$_{1-2}$ alkylcarbonyl, optionally substituted C$_{1-2}$ alkylsulfonamino, (C$_1$-C$_4$) alkylsulfinyl, optionally substituted C$_{1-2}$ alkylcarbonylamino, and optionally substituted hetero(C$_4$-C$_6$) aryl.

7. A method according to claim 1, wherein R$_1$, R$_2$, R$_4$, R$_5$, R$_6$, R$_7$, R$_8$, R$_9$, and R$_{10}$ are independently selected from the group consisting of optionally substituted C$_{1-4}$ alkyl, optionally substituted C$_{2-4}$ alkenyl, and optionally substituted C$_{2-4}$ alkynyl.

8. A method according to claim 1, wherein the compound has the general formula (II):

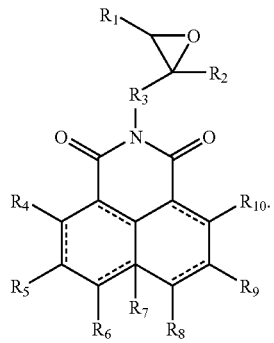

(II)

9. A method according to claim 1, wherein the compound has the general formula (III):

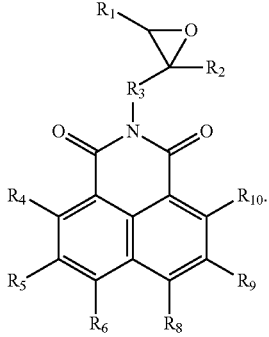

(III)

10. A method according to claim 1, wherein the compound has the general formula (IV):

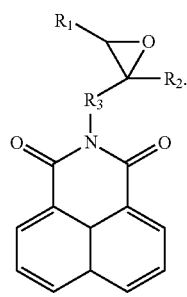

(IV)

11. A method according to claim 1, wherein the compound has the general formula (V):

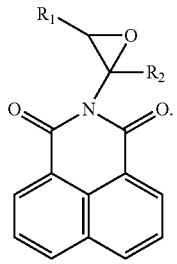
(V)

12. A method according to claim 1, wherein the compound has the formula (VI):

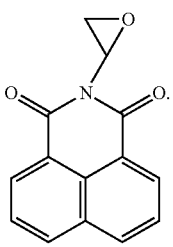
(VI)

13. A method according to claim 1, wherein the compound has the formula (VII):

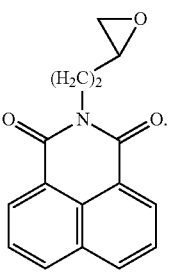
(VII)

14. A method according to claim 1, wherein the compound has the formula (VIII):

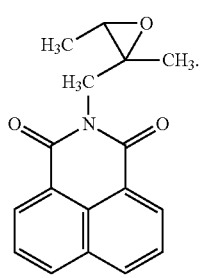
(VIII)

15. A method according to claim 1, wherein the compound has the formula (IX):

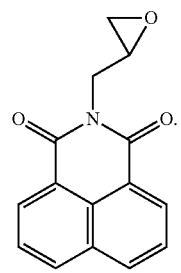
(IX)

16. A method according to claim 1, wherein the compounds are selected from the group consisting of: 2-(2-oxiran-2-ylethyl)-1H-benzo[de]isoquinoline-1,3 (2H)-dione; 2-[(3-methyloxiran-2-yl)methyl]-1H-benzo[de]isoquinoline-1,3(2H)-dione; 2-[(2,3-dimethyloxiran-2-yl)methyl]-1H-benzo[de]isoquinoline-1,3(2H)-dione; 2-(oxiran-2-ylmethyl)-1,3-dioxo-2,3-dihydro-1H-benzo[de]isoquinolin-5-yl nitrite; and 2-(oxiran-2-ylmethyl)-1,3-dioxo-2,3-dihydro-1H-benzo[de]isoquinoline-5,8-diyldinitrite.

17. A method as claimed in claim 1, wherein the compound induces apoptosis in the targeted cell.

18. A method of treating a disease selected from cervical cancer, metastatic neuroblastoma and osteosarcoma, in a patient in need thereof, the method comprising administering a compound of general formula (I):

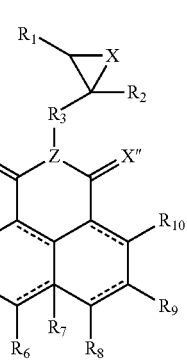
(I)

and the pharmaceutically acceptable salts, individual isomers and mixtures of isomers thereof, wherein X, X' and X" are independently O or S;

Z is N;

$R_3$ is optional and is selected from the group consisting of optionally substituted $C_{1-8}$ alkylene, optionally substituted $C_{2-6}$ alkenylene, and optionally substituted $C_{2-6}$ alkynylene;

$R_1$, $R_2$, $R_4$, $R_5$, $R_6$, $R_7$, $R_8$, $R_9$, and $R_{10}$ are independently selected from the group consisting of hydrogen, optionally substituted $C_{1-8}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ thioalkyl, optionally substituted $C_{5-10}$ aryl, optionally substituted $C_{6-11}$ alkylaryl, optionally substituted $C_{1-6}$ alkylamino, optionally substituted $C_{1-6}$ alkylcarbonyl, optionally substituted $C_{1-6}$ alkylsulfonamino, optionally substituted ($C_1$-$C_6$) alkylsulfinyl, optionally substituted $C_{1-6}$ alkylcarbonylamino, optionally substituted hetero ($C_4$-$C_{10}$) aryl, hydroxyl, halogen, cyano, nitro, amino, formyl, and thiol; and

- - - indicates an optional double bond.

19. A method as claimed in claim 18, wherein the patient is a mammal.

20. A method as claimed in claim 19, wherein the mammal is a human.

21. A method as claimed in claim 18, wherein the disease is cervical cancer.

22. A method as claimed in claim 18, wherein the disease is metastatic neuroblastoma.

23. A method as claimed in claim 18, wherein the disease is osteosarcoma.

* * * * *

UNITED STATES PATENT AND TRADEMARK OFFICE
CERTIFICATE OF CORRECTION

| | |
|---|---|
| PATENT NO. | : 8,188,112 B2 |
| APPLICATION NO. | : 11/887064 |
| DATED | : May 29, 2012 |
| INVENTOR(S) | : Surana Uttam et al. |

It is certified that error appears in the above-identified patent and that said Letters Patent is hereby corrected as shown below:

On the Title Page, under item (86) at §371 (c)(1),(2), (4) date: replace "Apr. 30, 2009" with -- Apr. 23, 2009 --

Signed and Sealed this
Eighteenth Day of December, 2012

David J. Kappos
*Director of the United States Patent and Trademark Office*